US010045907B2

(12) United States Patent
Harper et al.

(10) Patent No.: US 10,045,907 B2
(45) Date of Patent: Aug. 14, 2018

(54) DEVICE, SYSTEM AND METHOD FOR REDUCING HEADACHE PAIN

(71) Applicant: The Regents of the University of California, Oakland, CA (US)

(72) Inventors: Ronald M. Harper, Los Angeles, CA (US); Eberhardt K. Sauerland, Reno, NV (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 331 days.

(21) Appl. No.: 14/546,784

(22) Filed: Nov. 18, 2014

(65) Prior Publication Data

US 2015/0141879 A1  May 21, 2015

Related U.S. Application Data

(60) Provisional application No. 61/905,616, filed on Nov. 18, 2013.

(51) Int. Cl.
*A61H 23/00* (2006.01)
*A61H 23/02* (2006.01)
(Continued)

(52) U.S. Cl.
CPC ............ *A61H 23/02* (2013.01); *A61H 21/00* (2013.01); *A61M 21/00* (2013.01);
(Continued)

(58) Field of Classification Search
CPC ............ A61H 2205/027; A61H 21/00; A61H 2021/0022; A61H 23/00; A61N 1/36075;
(Continued)

(56) References Cited

U.S. PATENT DOCUMENTS 5,788,656 A * 8/1998 Mino ..................... A61F 11/00
                                                                     601/47
8,142,373 B1    3/2012 Riles
(Continued)

FOREIGN PATENT DOCUMENTS

JP    H09108355       4/1997
JP    2009022699      5/2009
WO    WO 2012/094484 A1 * 7/2012 ............... A61N 1/36

OTHER PUBLICATIONS

DaSilva et al. "tdCS-Induced Analgesia and Electrical Fields in Pain-Related Neural Networks in Chronic Migraine", 2012, The Journal of Head and Face Pain, 52:1283-1295.
(Continued)

*Primary Examiner* — Justine Yu
*Assistant Examiner* — Kathrynn Lyddane
(74) *Attorney, Agent, or Firm* — Riverside Law LLP

(57) ABSTRACT

A device for stimulating at least one cranial nerve and/or spinal nerve is described. The device includes a vibratory motor, and an earpiece, wherein the earpiece is molded substantially to fit within the external ear canal and contacting the concha of a subject's ear. A method of reducing migraine headache and trigeminal neuropathy pain is also described. The method includes positioning a vibratory earpiece within an ear of a subject, applying vibrational energy to at least a portion of the skin of at least one of the auditory canal, auricle and concha of the ear, thereby stimulating at least one sensory fiber of at least one of cranial nerve 5, cranial nerve 7, cranial nerve 9, cranial nerve 10, spinal nerve C2, and spinal nerve C3. A method to normalize breathing, normalize blood pressure, induce sleep, increase salivation, and improve vertigo, nausea, and visual dysfunction accompanying migraine is also described.

31 Claims, 21 Drawing Sheets

(51) Int. Cl.
*A61H 21/00* (2006.01)
*A61M 21/00* (2006.01)

(52) U.S. Cl.
CPC .......... *A61H 2201/0184* (2013.01); *A61H 2201/501* (2013.01); *A61H 2201/5002* (2013.01); *A61H 2201/5005* (2013.01); *A61H 2201/5012* (2013.01); *A61H 2201/5097* (2013.01); *A61M 2021/0022* (2013.01); *A61M 2205/18* (2013.01); *A61M 2205/3553* (2013.01); *A61M 2205/3584* (2013.01); *A61M 2205/3592* (2013.01); *A61M 2210/0662* (2013.01)

(58) Field of Classification Search
CPC ............ A61N 1/36053; A61N 1/36032; H04R 25/00; H04R 25/02; H04R 25/60
See application file for complete search history.

(56) References Cited

U.S. PATENT DOCUMENTS

| | | | |
|---|---|---|---|
| 2003/0195588 A1 | 10/2003 | Fischell et al. | |
| 2007/0106344 A1* | 5/2007 | Darley | A61N 1/36032 607/55 |
| 2007/0250145 A1* | 10/2007 | Kraus | A61H 39/002 607/136 |
| 2008/0004672 A1* | 1/2008 | Dalal | A61N 1/36114 607/44 |
| 2008/0249439 A1* | 10/2008 | Tracey | A61H 39/04 601/46 |
| 2010/0198282 A1* | 8/2010 | Rogers | A61F 7/007 607/3 |
| 2011/0066176 A1* | 3/2011 | Coole | A61B 17/56 606/198 |
| 2013/0142378 A1* | 6/2013 | Bravo Cordero | H04R 1/105 381/380 |
| 2013/0282070 A1 | 10/2013 | Cowan et al. | |
| 2013/0303953 A1 | 11/2013 | Lattner | |

OTHER PUBLICATIONS

Meng et al, "Migraine Prevention with a Supraorbital Transcutaneous Stimulator: A Randomized Controlled Trial", 2013 Neurology, 81:1102-1103.

Mosqueira et al., "Vagus Nerve Stimulation in Patients with Migraine" 2013, Rev Neurol, 57(2): 57-63; English Abstract.

Schoenen et al., "Migraine prevention with a supraorbital transcutaneous stimulator" 2013 Neurology, 0(8): 697-704.

Silberstein et al., "Botulinum Toxin Type A as a Migraine Preventive Treatment" 2000; The Journal of Head and Face Pain, 40:445-450.

Pedersen et al., "Neurostimulation in cluster headache: A review of current progress"; 2013; Cephalagia, 33(14): 1179-1193.

Olesen and Ashina, "Emerging Migraine treatments and drug targets" 2011, Trends in Pharmacological Sciences, 33(6): 352-359.

Janetta, "Neurovascular Compression in Cranial Nerve and Systemic Disease" 1980, Ann Surg, 192(4): 518-525.

Akerman, S., et al. "Pearls and pitfalls in experimental in vivo models of migraine: Dural trigeminovascular nociception." Cephalagia, 2013, 33 (8) 577-592.

Hu et al. "Burden of migraine in the United States: disability and economic costs." Arch. Intern. Med., 1999, 159, 813-818.

\* cited by examiner

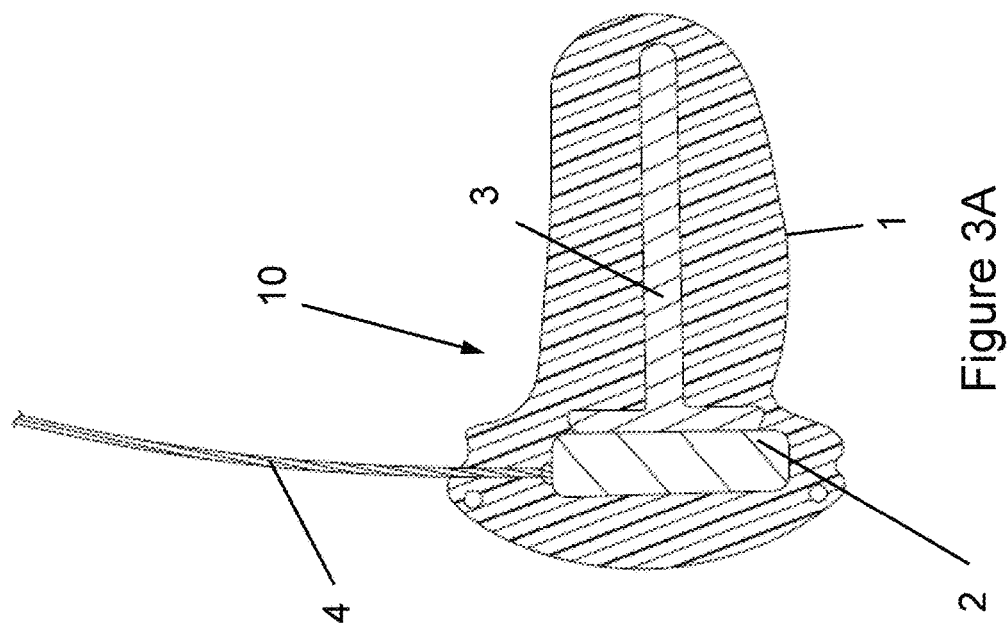
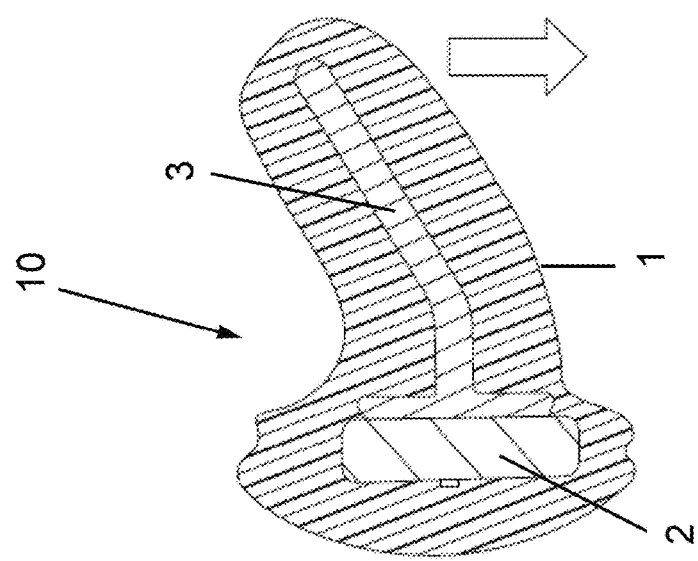

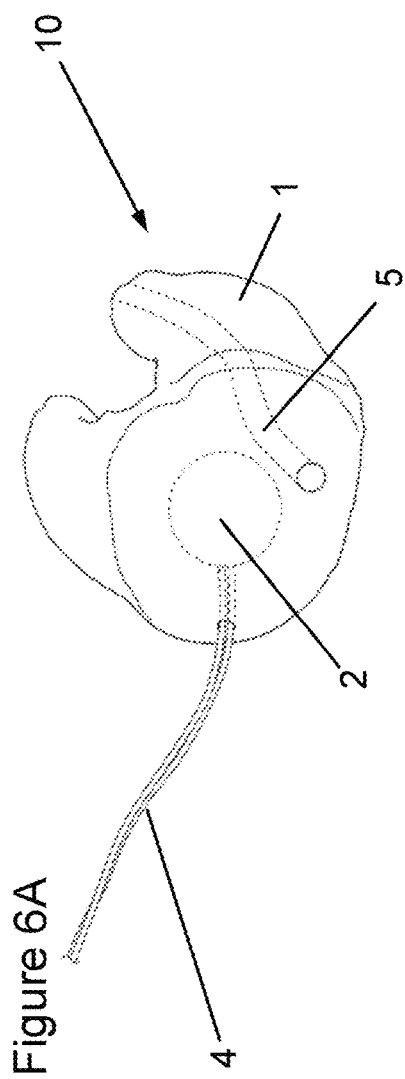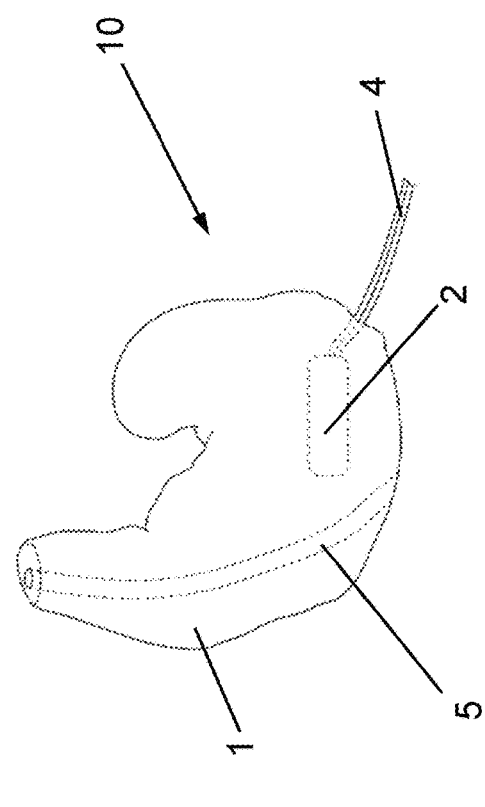
Figure 6A
Figure 6B

DEVICE, SYSTEM AND METHOD FOR REDUCING HEADACHE PAIN

CROSS-REFERENCE TO RELATED APPLICATIONS

This application claims priority to U.S. Provisional Patent Application No. 61/905,616 filed Nov. 18, 2013, the contents of which are incorporated by reference herein in their entirety.

BACKGROUND OF THE INVENTION

Migraine headaches affect approximately 9% (21 million female; 7 million male) of the population in the United States. The worldwide estimate of incidence is 650 million. There are a number of different forms of migraine. A principal characteristic of all migraines is recurrence, and the pain can be moderate to severe if left untreated. For example, the headache may be unilateral, can be triggered by light, sound, smells, or other stimuli, and is often accompanied by nausea, vestibular symptoms, and visual distortions, or preceded by an aura.

Interventions for migraine are difficult, since the pain may involve multiple central nervous system structures and neurotransmitters. In many instances, the autonomic nervous system is involved, which leads to nausea, vomiting, and cardiovascular signs, as well as headache. Other substantial variations in migraine appear, ranging from ocular pain accompanied by vision loss or blindness, muscle tension, sinus pain, and vertebrobasilar pain associated with vertigo. A variation of migraine pain is generally called "trigeminal neuropathy," and typically includes long-lasting oral pain, often arising from failed or compromised dental procedures, with trigeminal nerve (cranial nerve 5), facial nerve (cranial nerve 7), glossopharyngeal nerve (cranial nerve 9), or vagal (cranial nerve 10) irritation involved. The disorder can be accompanied by severe pain for many years, paraesthesias (such as tickling, odd sensations, or numbness), or sensations of burning. The so-called "burning mouth" syndrome, characterized by long-lasting, severe pain in the tongue or oral cavity i.e., stomatodynia and glossodynia, as well as severe, overwhelming pain from mild stimulation to the face, trigeminal neuralgia, also appears. These variations emphasize the complexity of migraine and associated pain syndromes.

Classical approaches to pain intervention include pharmacologic intervention, electrical stimulation, including transcranial electrical stimulation (DaSilva et al., 2012, The Journal of Head and Face Pain, 52: 1283-1295), electrical stimulation of the forehead, deep brain structures, or nerves within the brain or deep to the surface (Meng et al., 2013, Neurology, 81: 1102-1103; Mosqueira et al., 2013, Rev Neurol, 57(2): 57-63; Schoenen et al., 2013, Neurology, 0(8): 697-704), and Botox application (Silberstein et al., 2000; The Journal of Head and Face Pain, 40: 445-450) to reduce innervation to scalp muscles. Electrical stimulation of the peripheral skin poses a risk of injury to the underlying tissue, and can be uncomfortable. Outcomes of muscle paralysis procedures from Botox are often transient, and require skilled professional intervention, with careful attention to infection risk. The stimulation procedures requiring deep brain stimulation or access to nerves involve major surgery with substantial anesthetic and infection concerns (Pedersen et al., 2013; Cephalagia, 33(14): 1179-1193). Other procedures can vary in effectiveness. A range of pharmaceutical interventions exist (Olesen and Ashina, 2011, Trends in Pharmacological Sciences, 33(6): 352-359), and include serotonin agonists and nitric oxide antagonists. Many of these pharmaceutical interventions have severe side effects, including excessive sleepiness and addiction, especially to opioid agents. The impaired cognitive, arousal, gastric irritation, vestibular, and affective consequences of pharmaceutical agents pose concerns. Trigeminal neuralgia typically requires seizure medication, vascular decompression surgery, or lesioning of areas of the 5th cranial nerve (Janetta, 1980, Ann Surg, 192(4): 518-525). The invasiveness and severity of side effects make none of these options optimal.

Since migraine headaches involve multiple central nervous system (CNS) modulators, these classical approaches to pain intervention are not sufficiently targeted. There is thus a need for a migraine pain intervention via stimulation of multiple cranial nerves in a pattern that interferes with pain perception. Ideally, these stimuli would be non-invasive, and be patient-controllable, with the patient adjusting the stimuli when pain appears. The patient should also have the option to "condition" CNS processes to suppress migraine development, i.e. apply stimulation to "train" the brain to suppress brain activity that might lead to later migraine onset. Accordingly, there is a need in the art for alternative, non-invasive, devices and procedures that are easy to use for reducing headache pain and alleviating symptoms associated with migraine pain. The present invention satisfies this need.

SUMMARY OF THE INVENTION

In one aspect, the present invention relates to a device for stimulating one or more sensory fibers of a nerve. The device comprises an earpiece comprising a housing molded substantially to fit within the external ear canal and contacting the concha of a subject's ear; and a vibratory motor embedded within the housing, wherein the vibratory motor transmits vibrational energy to the outer wall of housing. In one embodiment, the earpiece is a customized silicon-plastic mold.

In one embodiment, the vibratory motor is connected to and powered by a control unit. In one embodiment, the control unit is controlled by a computing device. In one embodiment, the computing device controls the control unit wirelessly.

In one embodiment, the device comprises a vibrating rod having a substantially flat plate and an elongated arm, wherein the plate is in contact with the vibratory motor and the elongated arm extends away from the vibratory motor. In one embodiment, the elongated arm of the vibrating rod is an angled rod having between a 35-40° bend to match the curvature of the subject's ear canal. In one embodiment, the device comprises a hollow air duct running the length of the earpiece.

In one embodiment, the device stimulates one or more sensory fibers of at least one nerve selected from the group consisting of cranial nerve 5, cranial nerve 7, cranial nerve 9, cranial nerve 10, spinal nerve C2, and spinal nerve C3. In one embodiment, the device simultaneously stimulates one or more sensory fibers of cranial nerve 5, cranial nerve 7, cranial nerve 9, cranial nerve 10, spinal nerve C2, and spinal nerve C3.

In one aspect, the present invention relates to a device comprising an earpiece comprising a housing molded substantially to fit within the external ear canal and contacting the concha of a subject's ear; and a vibratory motor releasably coupled to the housing, wherein the vibratory motor transmits vibrational energy to the outer wall of housing. In one embodiment, the earpiece is a customized silicon-plastic mold.

In one embodiment, the vibratory motor is connected to and powered by a control unit. In one embodiment, the control unit is controlled by a computing device. In one embodiment, the computing device controls the control unit wirelessly.

In one embodiment, the earpiece comprises a magnet embedded within the housing. In one embodiment, device further comprises a magnet attached to the vibratory motor, such that the magnet of the motor releasably couples to the magnet of the housing.

In one embodiment, the device comprises a vibrating rod having an elongated arm, which extends away from the releasably coupled vibratory motor. In one embodiment, the elongated arm of the vibrating rod is an angled rod having between a 35-40° bend to match the curvature of the subject's ear canal. In one embodiment, the device comprises a hollow air duct running the length of the earpiece.

In one embodiment, the device stimulates one or more sensory fibers of at least one nerve selected from the group consisting of cranial nerve 5, cranial nerve 7, cranial nerve 9, cranial nerve 10, spinal nerve C2, and spinal nerve C3. In one embodiment, the device simultaneously stimulates one or more sensory fibers of cranial nerve 5, cranial nerve 7, cranial nerve 9, cranial nerve 10, spinal nerve C2, and spinal nerve C3.

In one aspect, the present invention relates to a method for non-invasively stimulating one or more sensory fibers of at least one of nerve. The method comprises positioning a vibratory earpiece within at least one ear of a subject and applying vibrational energy through the vibratory earpiece to at least a portion of the skin of at least one of the auditory canal, auricle and concha of the subject's ear. In one embodiment, the at least one nerve is selected from the group consisting of cranial nerve 5, cranial nerve 7, cranial nerve 9, cranial nerve 10, spinal nerve C2, and spinal nerve C3. In one embodiment, one or more sensory fibers of each of a plurality of nerves are stimulated simultaneously by the vibrational energy.

In one embodiment, the method reduces pain in at least one of the head, face, mouth, or neck of the subject. In one embodiment, the method enhances breathing of the subject. In one embodiment, the method normalizes blood pressure via stimulation of at least the $9^{th}$ and $10^{th}$ cranial nerves supplying the carotid sinus baroreceptors and aortic sensors. In one embodiment, the method increases saliva production in the subject.

In one aspect, the present invention relates to a non-invasive method of reducing headache pain in a subject. The method comprises positioning a vibratory earpiece within at least one ear of a subject and applying vibrational energy through the vibratory earpiece to at least a portion of the skin of at least one of the auditory canal, auricle and concha of the subject's ear, thereby stimulating one or more sensory fibers of at least one nerve of the subject. In one embodiment, the at least one nerve is selected from the group consisting of cranial nerve 5, cranial nerve 7, cranial nerve 9, cranial nerve 10, spinal nerve C2, and spinal nerve C3. In one embodiment, one or more sensory fibers of a plurality of nerves selected from the group consisting cranial nerve 5, cranial nerve 7, cranial nerve 9, cranial nerve 10, spinal nerve C2, and spinal nerve C3 are stimulated simultaneously by the vibrational energy.

In one embodiment, headache pain is reduced within 30 minutes after application of the vibratory energy. In another embodiment, headache pain is reduced within 10 minutes after application of the vibratory energy. In another embodiment, headache pain is reduced within 5 minutes after application of the vibratory energy.

BRIEF DESCRIPTION OF THE DRAWINGS

The following detailed description of preferred embodiments of the invention will be better understood when read in conjunction with the appended drawings. For the purpose of illustrating the invention, there are shown in the drawings embodiments which are presently preferred. It should be understood, however, that the invention is not limited to the precise arrangements and instrumentalities of the embodiments shown in the drawings.

FIG. 3, comprising FIG. 3A and FIG. 3B, are schematic illustrations of the frontal view (FIG. 3A) and top view (FIG. 3B) of an exemplary vibrating device with the internal vibrating motor and rod of the present invention. The rod is used to transfer vibration to the deepest recesses of the auditory canal.

FIG. 6, comprising FIG. 6A and FIG. 6B, are schematic illustrations of an exemplary vibratory earpiece with an air duct.

FIG. 10, comprising FIG. 10A shows the inserted ear piece with the embedded disc magnet and opening for the air canal. The motor with its magnet of opposite polarity is close but not yet attached. FIG. 10B shows that the magnetic vibrator has precisely latched onto its target.

FIG. 12, comprising

FIG. 13, comprising

DETAILED DESCRIPTION

Figure 1:
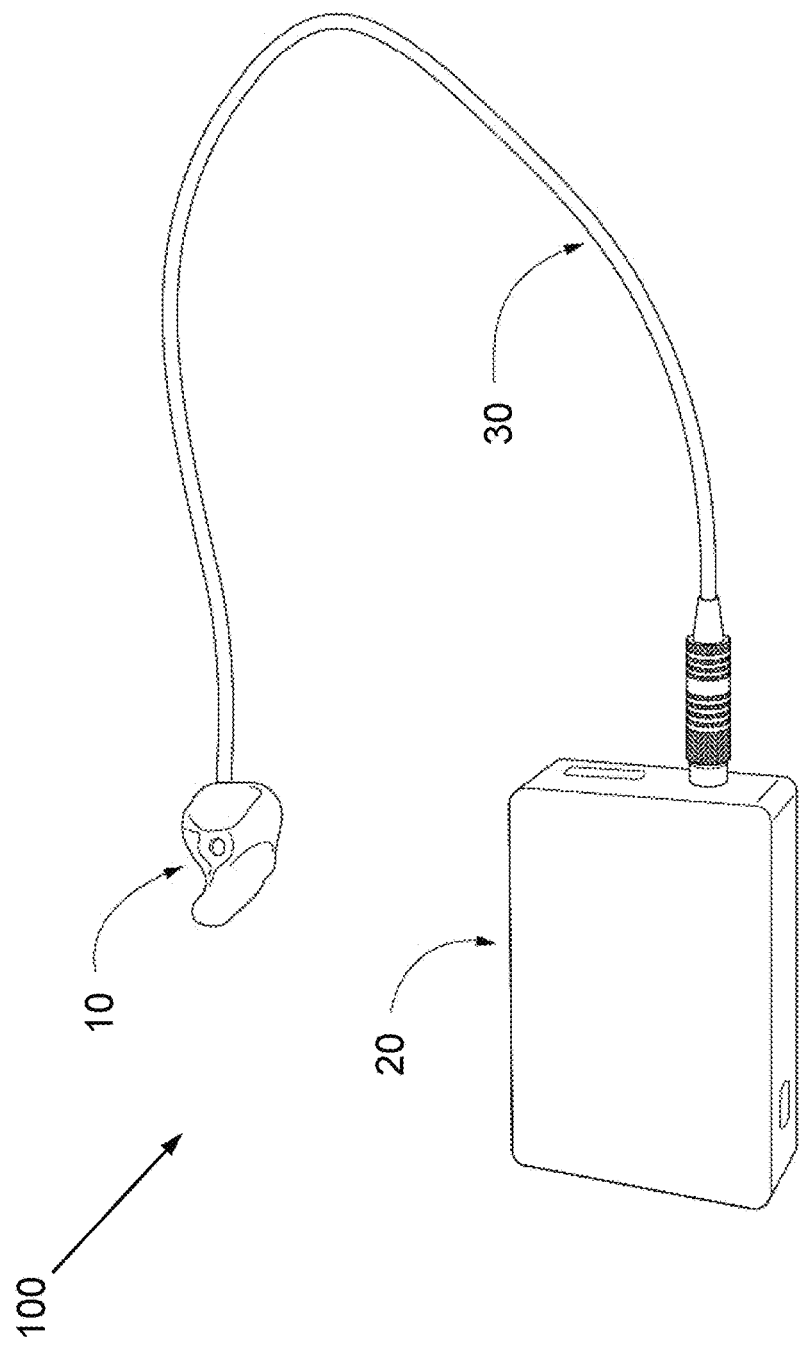
FIG. 1 is a schematic illustration of an exemplary programmable control unit and earpiece, coupled by an insulated wire.

It is to be understood that the figures and descriptions of the present invention have been simplified to illustrate elements that are relevant for a clear understanding of the present invention, while eliminating, for the purpose of clarity, many other elements found in typical devices, systems and methods for reducing headache and trigeminal neuropathy (oral-facial) pain. Those of ordinary skill in the art may recognize that other elements and/or steps are desirable and/or required in implementing the present invention. However, because such elements and steps are well known in the art, and because they do not facilitate a better understanding of the present invention, a discussion of such elements and steps is not provided herein. The disclosure herein is directed to all such variations and modifications to such elements and methods known to those skilled in the art.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20%, ±10%, ±5%, ±1%, and ±0.1% from the specified value, as such variations are appropriate.

Throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, 6 and any whole and partial increments therebetween. This applies regardless of the breadth of the range.

DESCRIPTION

The present invention includes a device, system and method that disrupt or inhibit central nervous system processes that mediate pain in the head or face by activating both the cranial nerve mediating that pain as well as other cranial nerves that use the same central nuclei which integrate pain processing. Since migraine headaches involve multiple central nervous system (CNS) modulators, the possibility exists to interfere with pain processes by distorting sensory input so as to confuse neural mechanisms normally mediating pain. The potential for confusing such processes is readily demonstrated by the poor brain discrimination of intense pain, such as that from a myocardial infarction ("heart attack"). The pain from the heart in such an attack is often referred to the arm, ear, jaw, or shoulder; such poor discrimination offers the possibility that other sensory input could confuse the brain for perception of pain.

The present invention utilizes mechanical vibration (as opposed to electrical stimulation) to activate these nerves through skin sensory receptors and mask pain perception. The vibratory stimuli of the present invention are non-invasive and patient-controllable, such that the subject may make real-time adjustments to the amplitude and timing of the stimuli when pain appears. In some embodiments, the subject may "teach" or "condition" selected CNS processes to suppress migraine development. For example, the subject may apply vibration to "train" the brain to suppress brain activity that would otherwise lead to later migraine onset. Further, as described elsewhere herein, vibrational activation of these cranial nerves also serves to treat hyposalivation, hypotension, hypertension, and visual and vestibular disturbances related to migraine in subjects in need.

Much of cranial pain, including oral pain, is mediated by the $5^{th}$ cranial (trigeminal) nerve which integrates pain through one of its nuclei, the descending spinal nucleus. That nucleus also mediates pain from other cranial nerves, 7, 9, and 10, as well as from two spinal (cervical) nerves of the posterior scalp, C2 and C3. It should be appreciated that each or all of these cranial and cervical nerves can contribute to the sensation of pain in various forms of migraine. As contemplated herein, the device and system of the present invention activates sensory fibers of cranial nerves 5, 7, 9, and 10, and cervical nerves C2, and C3, and disrupts activity of cranial nerve 5 by masking pain in its descending nucleus, or in insular cortical and other brain sites that integrate pain and other sensory signals, including vibration signals. Activity of the other cranial nerves can be similarly disrupted.

Such stimulation of 7, 9, 10, C2, and C3 has traditionally not been considered feasible, because these nerves are largely inaccessible, lying deep below the skin surface and being widely dispersed over the head and neck. However, the present invention is at least partially based on the discovery that a site exists where those nerves are in close proximity and innervate the surface in one area. As demonstrated herein, that area lies within the external auditory canal and extends to the auricle and concha. In fact, this site for administration of vibratory stimuli is the only site in the body in which the cranial nerves 5, 7, 9, 10 and spinal nerves C2 and C3 converge at an easily-accessible skin surface.

Vibrations produced by the device, system, and method of the present invention activate cutaneous mechanoreceptors in the external ear and ear canal. These tactile corpuscles (Meissner corpuscles) respond rapidly to mechanical skin changes, such as vibrations. The resulting nerve activities (in the form of electrical action potentials) enter the brain stem. Subsequently, they appear to inhibit incoming pain stimuli from various regions of the head and neck.

Accordingly, the present invention includes a method of stimulating one or more sensory fibers of at least one of cranial nerves 5, 7, 9, and 10, and spinal nerves C2, and C3, comprising applying vibrational energy to at least a portion of the skin of at least one of the auditory canal, auricle and concha of a subject's ear. In another embodiment, the present invention includes a method of reducing headache or trigeminal neuropathy pain in a subject, comprising applying vibrational energy to at least a portion of the skin of at least one of the auditory canal, auricle and concha of the subject's ear, thereby stimulating one or more sensory fibers of at least one of cranial nerves 5, 7, 9, and 10, and spinal nerves C2, and C3. In another embodiment, multiple cranial nerves and/or spinal nerves are stimulated simultaneously. In one embodiment, headache or trigeminal neuropathy pain is reduced within 1 to 100 minutes after application of vibratory stimuli. For example, in certain embodiments, headache pain is reduced within 50 minutes, within 30 minutes, within 10 minutes, within 9 minutes, 8 minutes, within 7 minutes, within 6 minutes, within 5 minutes, within 4 minutes, within 3 minutes, within 2 minutes, or even within 1 minute. In certain embodiments, the headache pain is reduced in less than 1 minute.

The present invention makes use of the neuroanatomical principle that cranial nerves 7, 9, 10, and spinal nerves C2 and C3 use the spinal descending nucleus of cranial nerve 5 for pain mediation, allowing activation of nerves from 7, 9, 10, C2 and C3 to mask pain signals from cranial nerve 5. Accordingly, the multiplicity of cranial and spinal nerves allows the devices and methods of the present invention to mask pain signals from cranial nerve 5. In another embodiment, if pain results not from cranial nerve 5, but from C2 or C3 areas, as it may from tension of the neck muscles or the dura of the brain, or from regions supplied by 7, 9, or 10, as it may from sites in the face, oral cavity or pharynx, activation of sensory fibers in the remaining cranial or spinal nerves can also provide a similar masking effect. Cranial nerve 9, for example, mediates glossopharyngeal neuralgia (excruciating pain similar to trigeminal neuralgia, but with origins in the posterior oral cavity), and is also a target for the present invention, since vibration would excite nearby fibers in 5, 7, 10 and C2-C3 which could mask such glossopharyngeal neuralgia. Accordingly, the present invention provides a novel approach for masking glossopharyngeal neuralgia pain, and has been used in that context In one embodiment, the device and system of the present invention includes an earpiece, within which is contained a small vibrating motor (diameter 8-10 mm). In one embodiment, the vibrating motor is attached to a small metal rod (5-15 mm length, 2-4 mm diameter), angled in the caudal direction to accommodate the anatomy of the auditory canal. In one embodiment, the earpiece comprises an air duct running the length of the earpiece to allow for the establishment of air pressure equilibrium. In one embodiment, the motor is not contained within the earpiece itself, but is instead releasably coupled to the earpiece, for example using magnetic or adhesive coupling.

It should be appreciated that there are no limitations to the actual shape and/or dimensions of the earpiece molding, vibrating motor, rod, and duct. Moreover, in one embodiment, to reduce the extent of vibration to the innermost portions of the auditory canal, the rod can be eliminated. Preferably, the device fits within the subject's ear such that the tip of the device extends immediately beyond the junction of the cartilaginous part of the ear canal and the temporal bone (the "Junction" in FIG. 11), but short of the tympanic membrane. While not required, custom molding is preferred, because the configurations of ear canals may differ greatly from subject to subject, and appropriate contact with the skin tissue inside the canal and concha is needed to enhance activation of the sensory nerves innervating the tissue.

Figure 4:
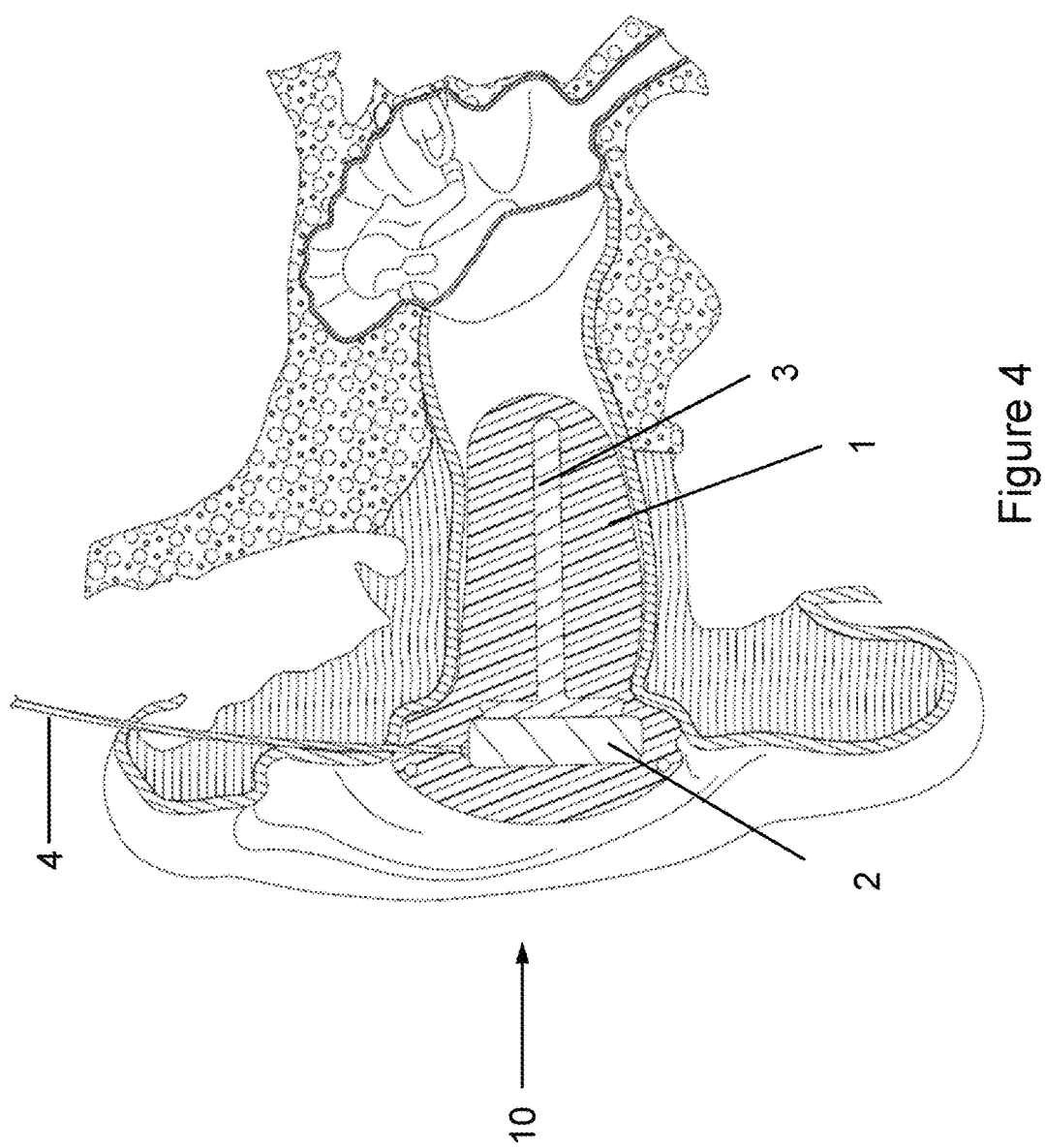
FIG. 4 is a schematic illustration of an exemplary vibrating device with metal rod for increased vibratory intensity inserted into the external ear canal. This version will be used in patients who require vibration that extends optimally to the deepest recesses of the auditory canal.

When the vibration motor is activated, vibrational energy is transferred to the metal rod, and subsequently the metal rod conveys the vibrational energy to the wall of the earpiece molding, which is adjacent to, and at least in partial contact with the tissue containing the cranial sensory nerves (FIG. 4 and FIG. 12). Where less-extensive vibration is needed to deeper portions of the auditory canal, the metal rod can be omitted. For example, in certain embodiments, the motor itself is sufficient to deliver the vibrational energy throughout the earpiece. Vibrations are also transmitted through the cartilaginous tissue to the concha and auricle (FIG. 4), recipient of nerve fibers from cranial nerves 5, 7, 9, 10, and spinal nerves C2 and C3 (FIG. 12 and FIG. 13). Activation of the cranial and the two spinal nerves will mask pain perception, principally from cranial nerves 5 and 9, but also from other cranial nerves by projection of the activated nerve signals to the descending spinal nucleus of 5, and to other brain structures (FIG. 12 and FIG. 13).

Figure 11:
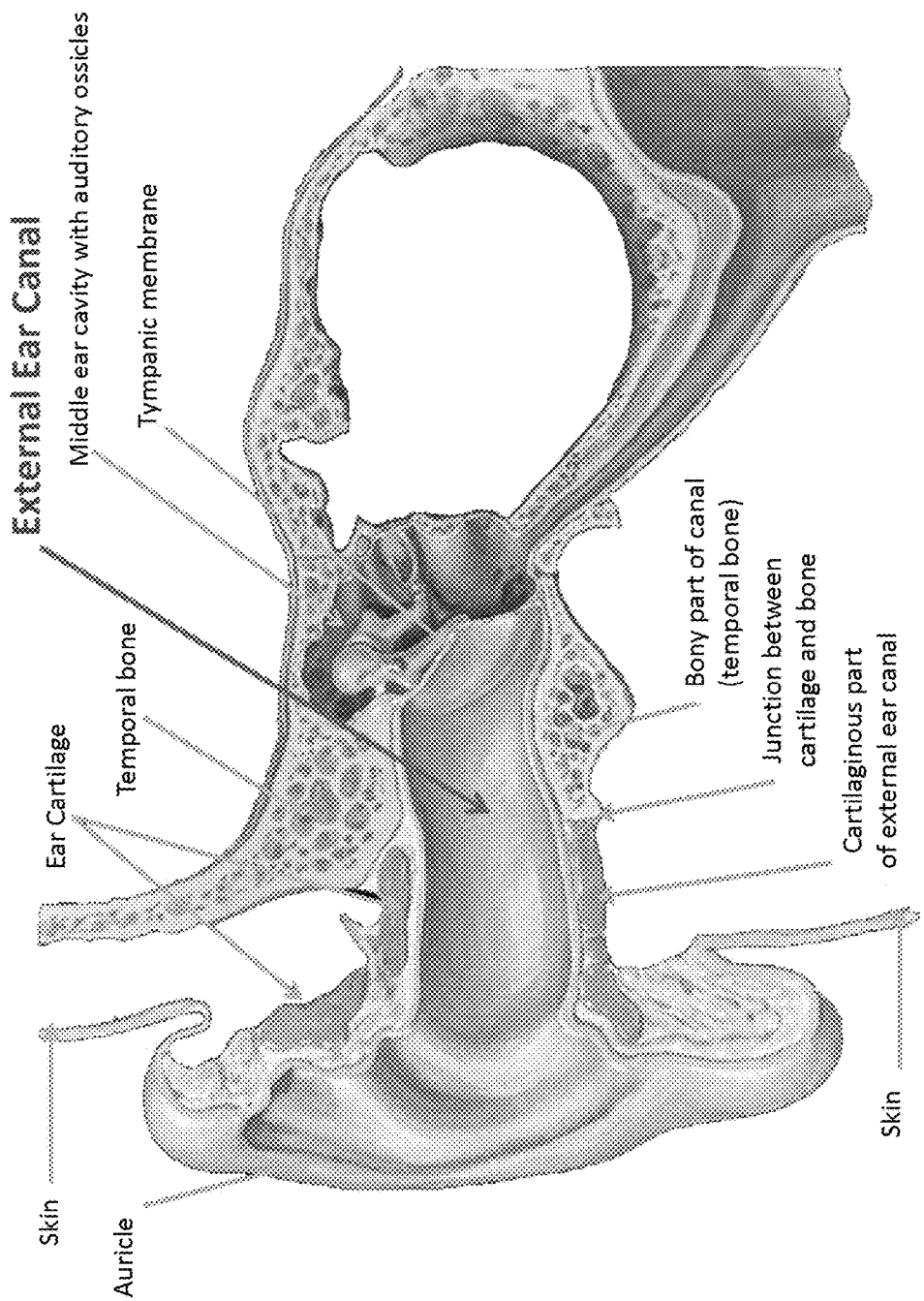
FIG. 11 is a schematic of a cross-sectional (coronal) view through the external ear canal and auricle, showing the major structures affected by the device of the present invention.

FIG. 11 is a cross-sectional view through the external ear canal and auricle, showing the major structures affected by the device of the present invention. The device preferably reaches the temporal bone just past the junction of the cartilaginous portion of the external ear canal, and may also come in contact with the bony part, and avoid reaching the tympanic membrane (eardrum). The device forms a close seal in the remaining portion of the external auditory canal and concha.

Figure 12B:
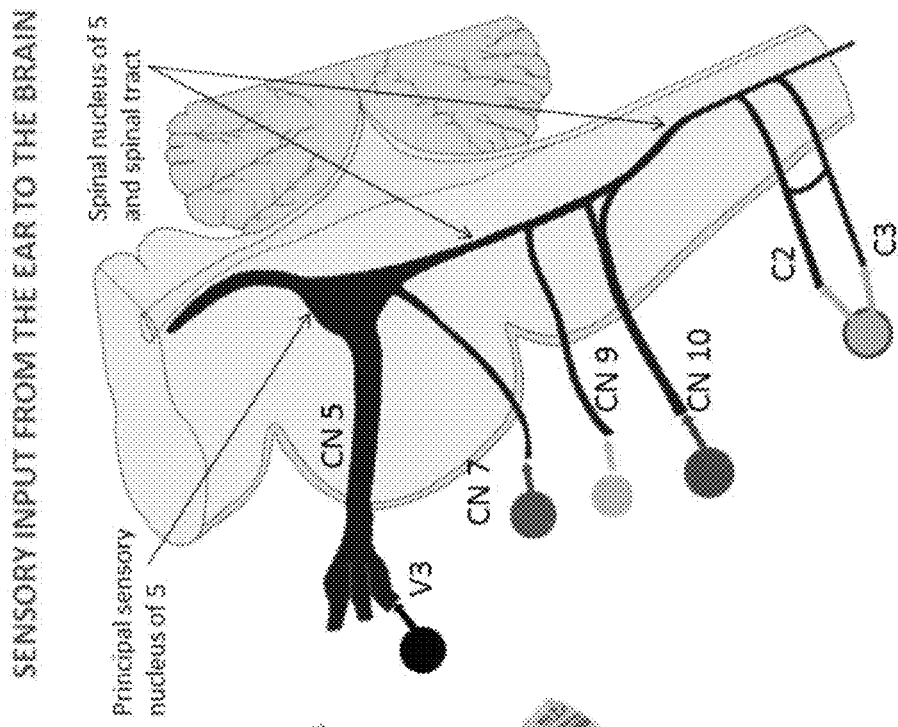
FIG. 12A and FIG. 12B, is an illustration of sensory input from the ear to the brain through multiple cranial (cranial nerves, CN 5, 7, 9, and 10), and C2 and C3 spinal nerves. The figure also shows that the sensory input for pain projects to a common nucleus, the spinal nucleus of 5 and spinal tract. The common input assists in confusing the brain into misperceiving a pain stimulus by using the proposed vibration to stimulate the multiple nerves simultaneously with an innocuous vibration. The ear is shown in coronal view.
Figure 12A:
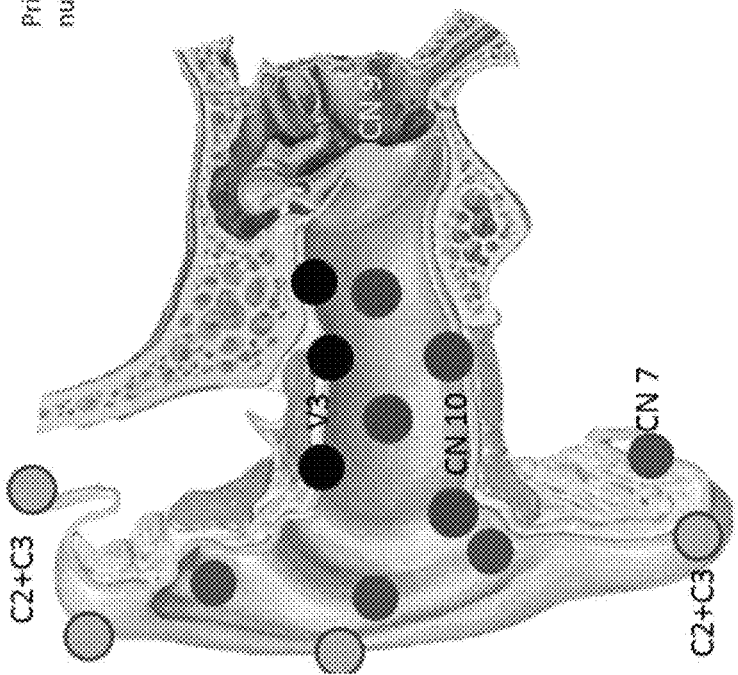
Figures 13A, 13B:
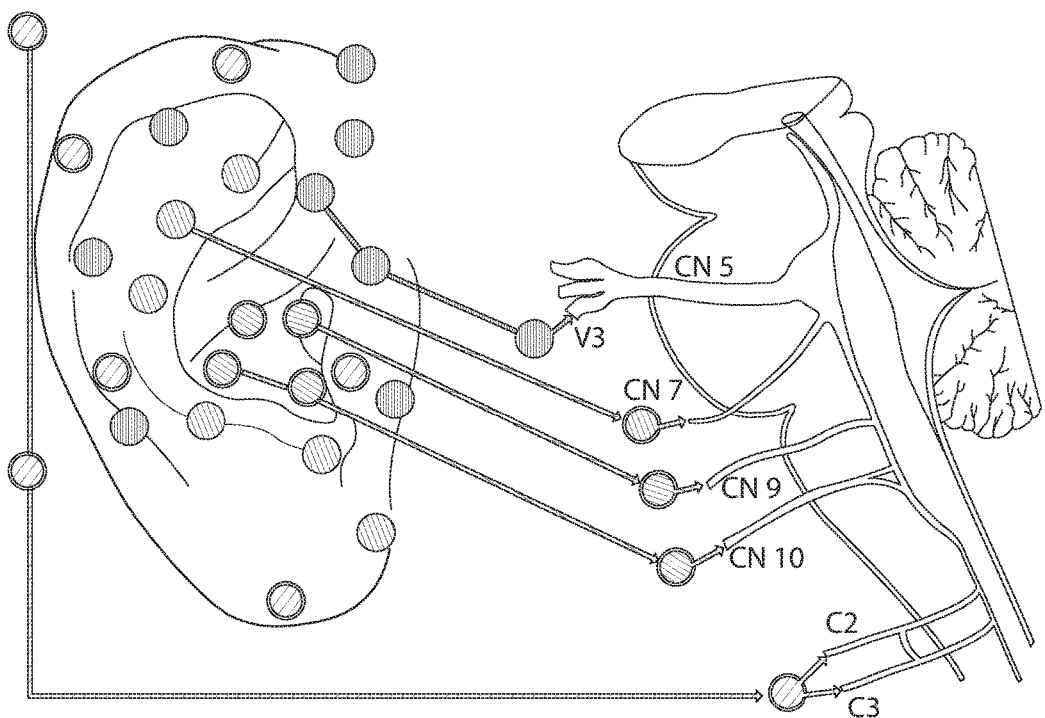
FIG. 13A and FIG. 13B, is another illustration of sensory input from the ear to the brain, and illustrates the large number of cranial nerves (5, 7, 9, and 10), and spinal nerves (C2 and C3) that can be stimulated with the device, with a number of those cranial nerves represented on the concha as well as the ear canal. The external ear and the ear canal are shown in lateral view.

FIG. 12A is an illustration of sensory input from the ear concha and the external ear canal to spinal nerves C2, and C3, and cranial nerves 5, 7, 9 and 10. The external ear canal (external acoustic meatus) is mainly supplied by the third division of cranial nerve 5, cranial nerves 10 and 9; the last serves the area of the tympanic membrane. Vibratory stimuli are transferred from the external ear canal to the tympanic membrane. FIG. 12B is an illustration of the brain stem nuclei involved in sensory information processing of the trigeminal nerve. The principal, or main sensory nucleus of cranial nerve 5 mediates touch, vibration, and pressure, but pain is mediated by the descending or spinal nucleus of 5, which is contiguous with the spinal tract mediating pain from lower nerves. FIG. 12A and FIG. 12B illustrate how pain mediated by cranial nerves 7, 9, 10 and spinal nerves C2 and C3 use the same descending spinal nucleus and spinal tract. FIG. 13A illustrates sensory input from the ear auricle, concha and the external ear canal to C2, C3, and cranial nerves 5, 7, 9 and 10. The external ear canal (external acoustic meatus) is mainly supplied by cranial nerve 5 ($V_3$), 7, and 10, and spinal nerves C2 and C3 contribute to the innervation of the auricle. Cranial nerve 9 supplies the area of the tympanic membrane. Vibratory stimuli from the external ear canal are transferred to the tympanic membrane. FIG. 13B illustrates brain stem nuclei as similarly depicted in FIG. 12B.

Device and System

The device and system of the present invention may be further described in light of and in reference to the following Figures.

Figure 2:
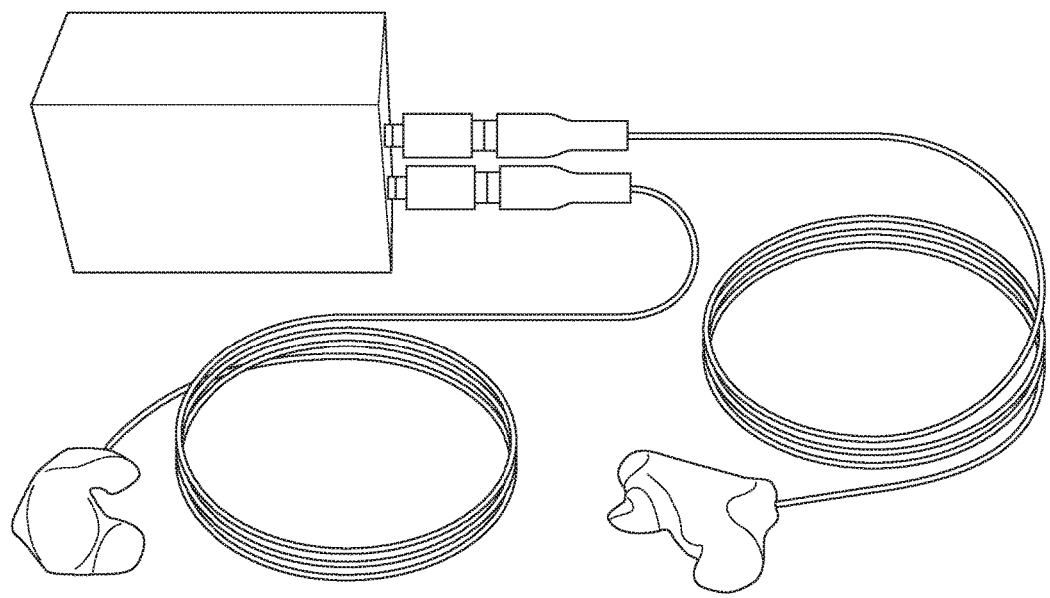
FIG. 2 is a photograph of an exemplary programmable control unit with two earpieces, coupled by insulated wire, and demonstrating the positions of patient-controllable up and down buttons in the middle surface of the control that can control the intensity of vibration of the vibrating motors. The control unit is programmed using a computing device to frequency, overall intensity, patterning of vibrating pulses, and overall duration of stimulation session.

As depicted in FIG. 1, the present invention provides a device 100 comprising an earpiece 10 and control unit 20. Earpiece 10 has a geometry which allows for its insertion into the exterior ear canal(s) of the subject. For example, in certain embodiments, earpiece 10 may be constructed from an impression of the subject's left and/or right ear canals and adjacent concha. Control unit 20 may include the battery power, vibratory stimulation programming electronics, switches to establish settings of stimulus pulse duration, frequency and pattern, and a display screen to indicate appropriate stimulation characteristics. In certain embodiments, control unit 20 comprises one or more output jacks for cables to send and/or receive information to earpiece 10. In certain embodiments, the device comprises two earpieces, each attached to a control unit via cables connected to two output jacks (FIG. 2).

In certain embodiments, control unit 20 is a programmable unit used to deliver electrical pulses to earpiece 10. In certain embodiments, control unit 20 is in wired communication with earpiece 10 via cable 30. In one embodiment, cable 30 is an insulated cable. For example, in one embodiment, control unit 20 is electrically connected to earpiece 10 via a cable or wire 30, as shown in FIG. 1. In other embodiments, earpiece 10 includes a wireless receiver and a power source such that earpiece 10 may wirelessly receive signals from control unit 20 and/or a computing device.

Control unit 20 may be powered by an internal battery, and uses that battery to send stimulation pulses, typically of a voltage of 1.5-5.0 volts. Alternatively, it may include a plug for accessing electricity from a home, hospital or other location providing access to an electrical power source.

In one embodiment, control unit 20 is used to set or alter the amplitude, pulse rate, pulse burst duration, interburst interval and any other parameter of applied vibrational energy, as desired. In one embodiment, vibration may be at a rate of about 20-200 Hz. In another embodiment, the vibration rate may be at about 120-160 Hz. In other embodiments, the rate of pulses and the duration of pulses may be patient- and/or condition-dependent. The total duration of a stimulation session may be established for periods ranging from 1-2 minutes to 60 minutes or more. The bursts of pulses may be set for varying intervals, for example to match the duration and timing of an inspiration or expiration when the device is used for overcoming sleep-disordered breathing. The timing of pulses within bursts can be set to vary between approximately 30-160 Hz for conditions that patients may feel more comfortable.

The amplitude of vibration can be adjusted for effectiveness of intervention and comfort. In one embodiment, amplitude of voltage to the vibratory motor for may be varied from 1.5 volts to 5 volts by the patient. Control unit 20 may comprise two or more output channels such that two or more stimulation pulses can be outputted as desired.

In one embodiment, control unit 20 can be switch-programmed to vary such characteristics. For example control unit 20 may comprise one or more depressible buttons, dials, recessed switches or a touch screen through which control unit 20 may be programmed by a user. The application layer of control unit 20 makes certain parameters accessible and modifiable by user. Control unit 20 may include a user interface including a display screen to provide text or other graphics indicating user information, such as pulse parameters of amplitude and intervals, battery power level, and the like.

Earpiece 10 may be placed within the external ear canal, and also contacting the concha for administration of a vibratory stimuli. Vibration may be induced by low-level battery power via an embedded power source or an external control unit, and transmitted to the sensory nerves lining the external auditory canal and concha, and further transmitted to sensory nerves of the auricle through the cartilaginous tissue of the external ear. Activation of the sensory nerves by vibration masks headache pain, which typically arises from the $5^{th}$, $7^{th}$, $9^{th}$ and $10^{th}$ cranial nerves, and C2 and C3 spinal nerves. Vibration can be initiated by the subject, and amplitude and pulse rate stimulation self-varied by the subject to minimize pain and maximize comfort.

In one embodiment, earpiece 10 comprises a housing 1. Housing 1 may be made from any suitable material including, but not limited to, soft or hard silicon-plastic. In one embodiment, housing 1 is a molded housing, where the mold may be derived from an impression the subject's ear. These impressions may then be converted to a custom vibration unit. In certain embodiments, device 100 comprises two separate earpieces 10, one for each of the user's ear. Thus in one embodiment, housings 1 of earpieces 10 may comprise a molded housing of the user's left ear and a molded housing of the user's right ear. In one embodiment, the impression of the user's ear(s) may include the concha, providing a larger volume for the mold on the ear canal opening. The interior of the mold is filled with silicon-plastic material to effectively carry vibrations to the outer wall of housing 1, allowing stimulation of the surrounding nerves, and carrying vibrations to the cartilaginous tissue and skin of the of the cavity of the concha and adjacent parts of the auricle where cranial nerves 10, 9, 7, 5, and spinal nerves C2 and C3 are represented. Thus, housing 1 of earpiece 10 may be custom-constructed from hard, inert silicone or similar non-tissue irritating material for each subject's ear using conventional earpiece impression procedures understood by those skilled in the art for construction of hearing aids. FIG. 4 depicts an exemplary earpiece 10 positioned in the external auditory canal and concha. As shown in FIG. 4, earpiece 10 does not reach the tympanic membrane (eardrum). Thus, in certain embodiments, the impression used to construct the earpiece mold may use a medially positioned layer of cotton to prevent direct contact with the tympanic membrane. In another embodiment, housing 1 of earpiece 10 may be pre-fabricated using standard sizes and geometries of the ear of the mammal (e.g., human, primate, dog, etc.) of which the device is intended for use.

In one embodiment, as illustrated in FIG. 3A and FIG. 3B, earpiece 10 comprises housing 1 within which a vibrating motor 2 is housed. When activated, motor 2 transmits vibrational energy through housing 1 and delivers vibrational energy to the outer wall of housing 1, thereby providing vibratory stimuli to the skin in contact with earpiece 10. Motor 2 may be a small, circular vibrator with a diameter of approximately 2-10 mm. It should be appreciated that vibration motor 2 may be of any type, size or dimension as understood by those skilled in the art, provided the vibrator is capable of neural stimulation, as described herein. For example, in one embodiment, motor 2 is a coin motor.

In one embodiment, vibration motor 2 is housed in an accessible compartment within housing 1. For example, in one embodiment, housing 1 comprises a hinge which allows access to the compartment for replacement of motor 2. In another embodiment, the compartment may be accessed via the removal of one or more screws which allows for removal of a portion of housing 1.

In some embodiments, as shown in FIG. 3, earpiece 10 comprises a metal vibration rod 3, which is attached to vibrating motor 2. Vibrating rod 3 includes a relatively flat head which attaches to or otherwise contacts vibrating motor 2, and an angled rod, with a 35-40° bend in the posterior direction to match the curvature of the ear canal. It should be appreciated that rod 3 may be angled at greater or lesser angles, and of any desired length and diameter, depending on the dimensions most comfortable for placement within any particular subject's ear. Moreover, as described below, and as shown in FIG. 5 and FIG. 6, rod 3 may be eliminated entirely when the solid material of housing 1 needs to convey vibrations principally to less-deep portions of the auditory canal.

In one embodiment, vibration motor 2 is coupled to a wire 4. In certain embodiments, wire 4 is coupled to cable 30, which connects earpiece 10 to control unit 20. In another embodiment, vibrational motor 2 is wirelessly connected to control unit 20 or to an external computing device, as described elsewhere herein.

Figure 5:
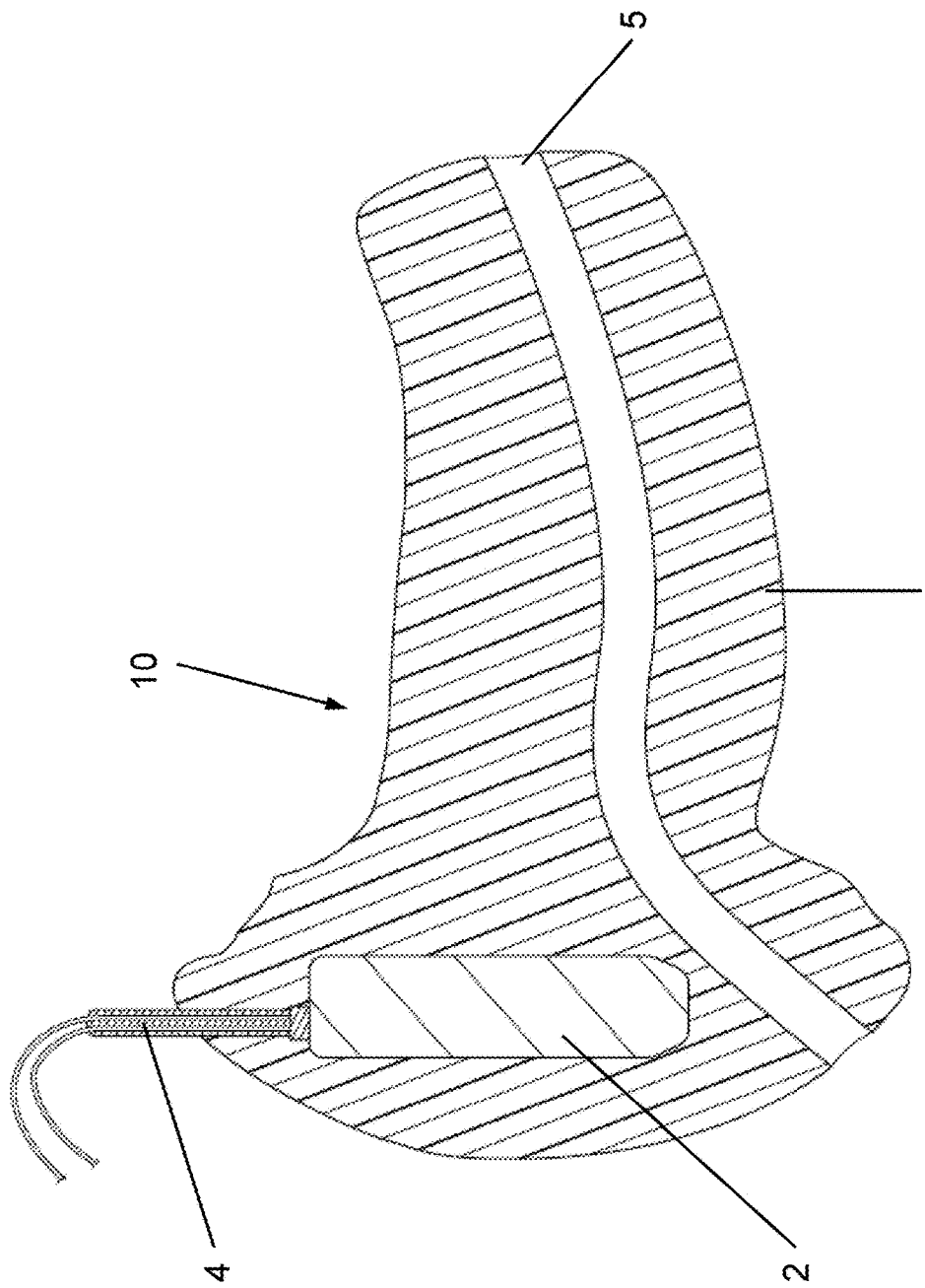
FIG. 5 is a schematic illustration of an exemplary vibrating device of the present invention with the vibrating motor and an air duct, but without an internal vibrating rod. In certain embodiments where the rod is absent, the vibrations are carried evenly to all parts of the device. The air duct ensures an identical atmospheric pressure on the outside and the inside of the inserted device.
Figure 7:
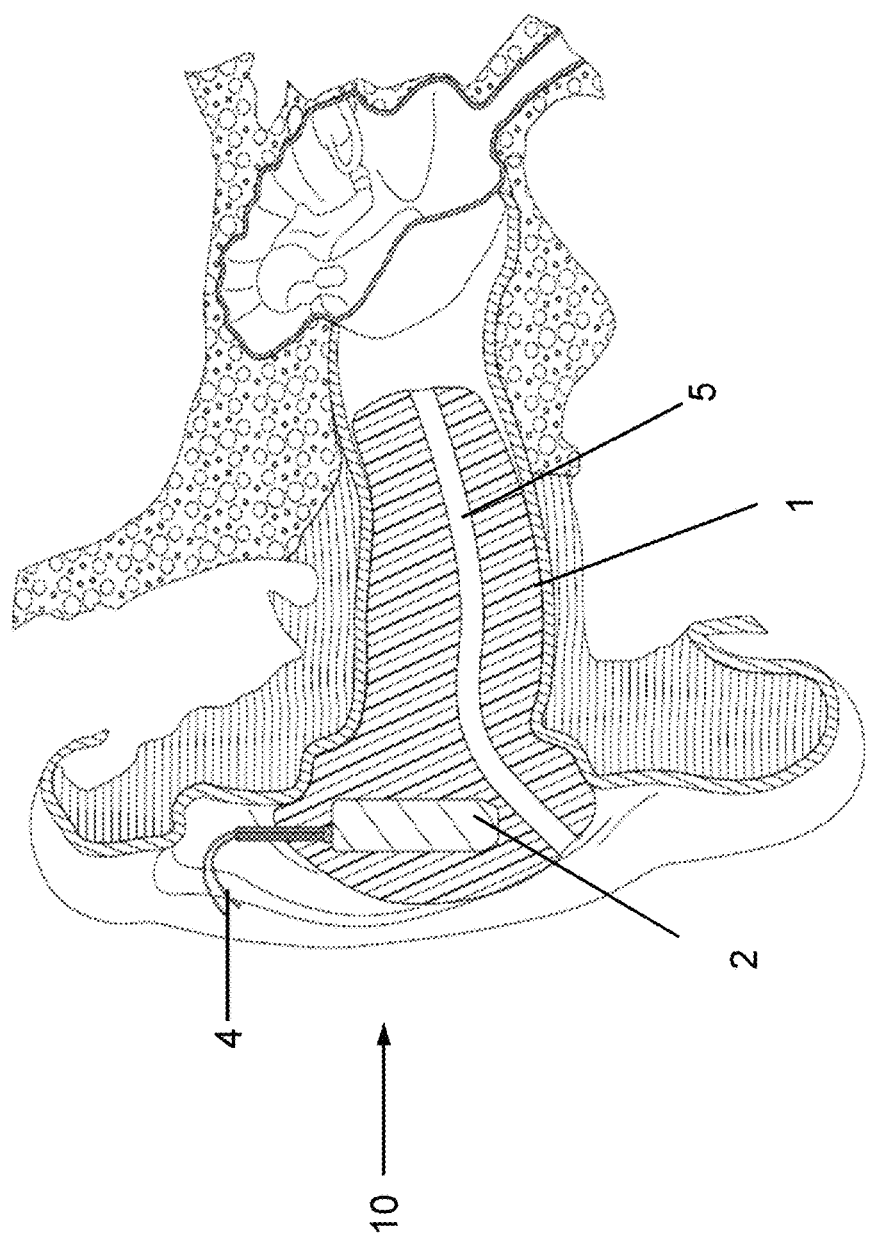
FIG. 7 is a schematic illustration of an exemplary vibrating device, comprising an air duct, inserted into the external ear canal. The air duct allows for the establishment of air pressure equilibrium.
Figure 8:
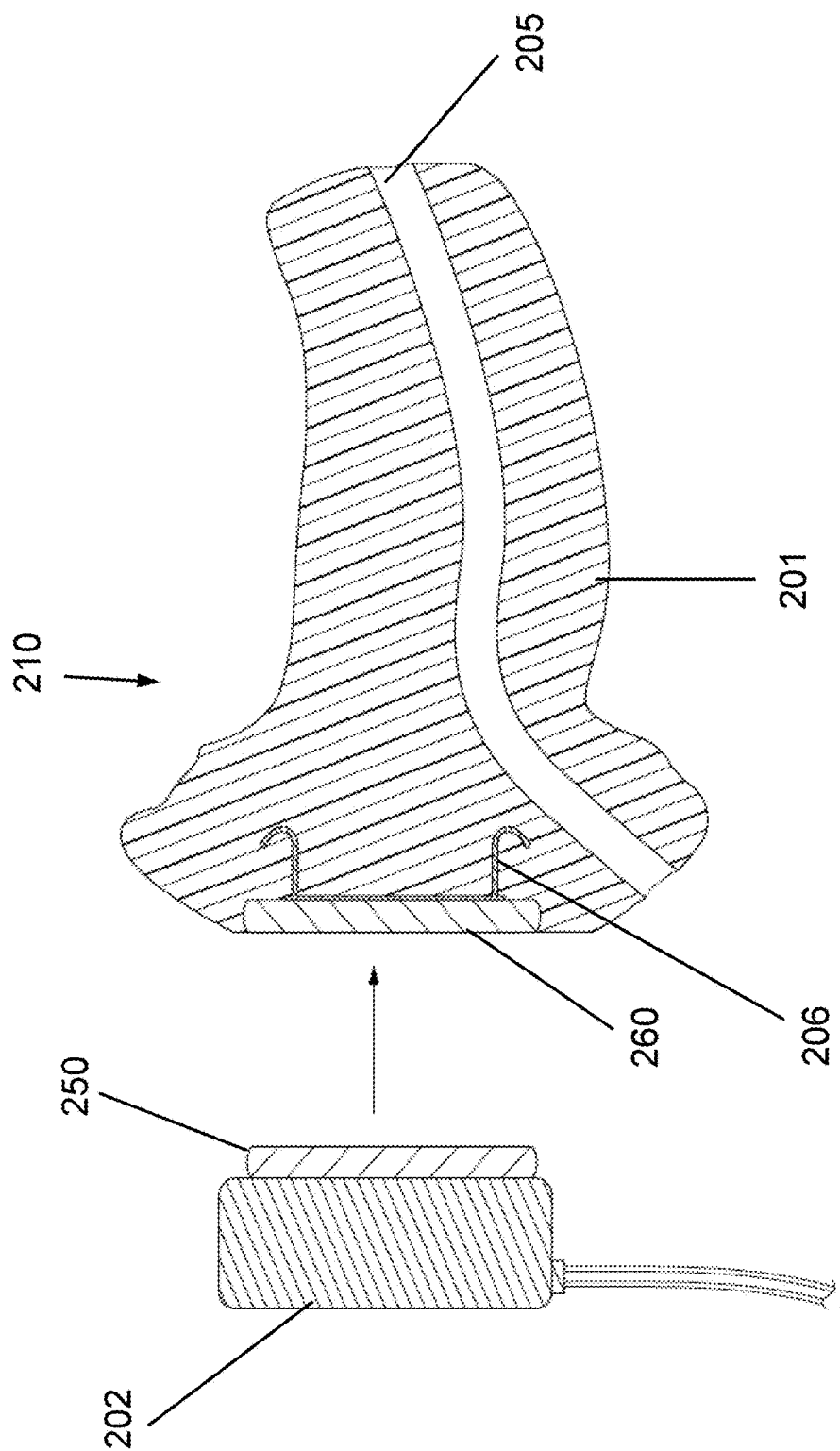
FIG. 8A is a schematic illustration of an exemplary device, where the earpiece comprises a disc magnet at its proximal end which is able to be magnetically coupled to a magnet of opposite polarity attached to a vibratory motor. Thus, in this embodiment, the motor need not be embedded or housed within the earpiece itself, but rather can be releasably coupled to the earpiece as desired.
FIGS. 8B and 8C are schematic illustrations of an exemplary device including a vibrational rod.

In one embodiment, as illustrated in FIG. 5-FIG. 7, earpiece 10 comprises a duct 5 which runs through the length of housing 1. Duct 5 allows for the establishment of air pressure equilibrium between the outside air and the ear duct at the tympanic membrane. Duct 5 may be of any suitable geometry and size which allows for the establishment of air pressure equilibrium. Duct 5 comprises an opening at the distal end of the housing, positioned near the tympanic membrane of the ear canal when earpiece 10 is inserted in the ear of the user, and an opening at the proximal end of the housing positioned at the external opening of the ear canal.

Figure 10A:
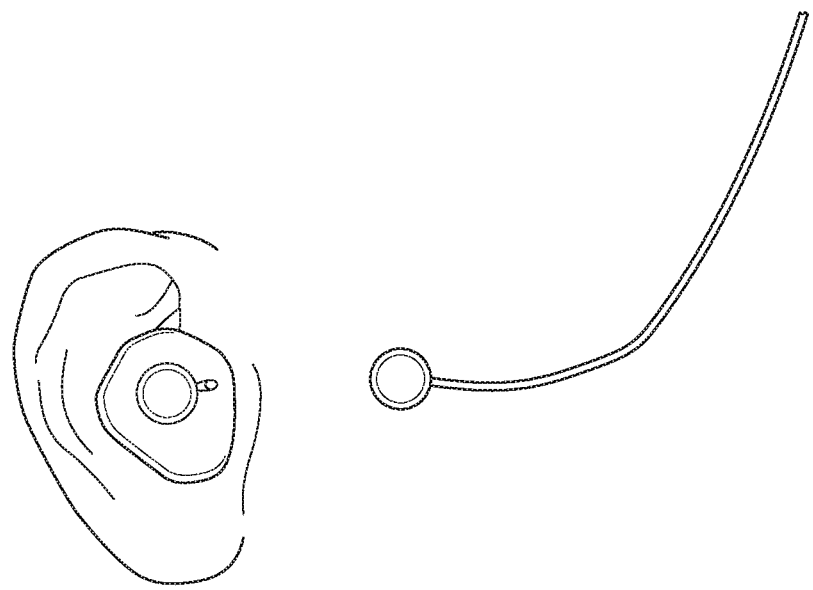
FIG. 10A and FIG. 10B, depicts a subject in the process of attaching the two device parts without visual control.
Figure 10B:
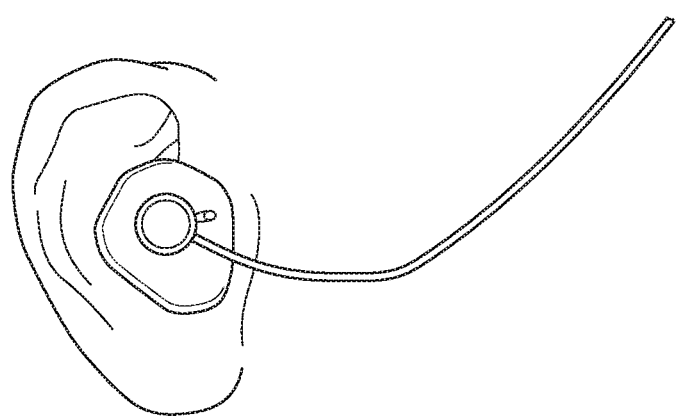

In one embodiment, the device is comprised of two separate components, where one component comprises an ear piece containing an embedded and well anchored magnet and the other component comprising a vibratory motor which is fused with a magnet. In certain embodiments, the magnet of the earpiece and magnet of the motor have opposite polarity. For example, in one embodiment, the magnet embedded within the earpiece has a default magnetic polarity of south while the magnet fused to the motor has a default magnetic polarity of north. When the two components are in close proximity, the two magnets automatically latch onto each other and establish a precise and firm connection between the vibrating motor and the earpiece. FIG. 10 demonstrates how a subject can connect the two parts of the device without visual control. It should be appreciated that the transmitted vibrations have the same strength and the same physiological effect as the device with the vibrating coin motor directly embedded into the ear piece, described elsewhere herein. In certain instances, this embodiment has several advantages. The separate ear piece that is tailored to a given patient's ear displays enhanced durability. The external and cabled vibratory motor component finds its desired position automatically, but it can be easily removed by sliding action. The vibrating motor component can be easily replaced, and it can also serve any other ear devices.

Figure 9:
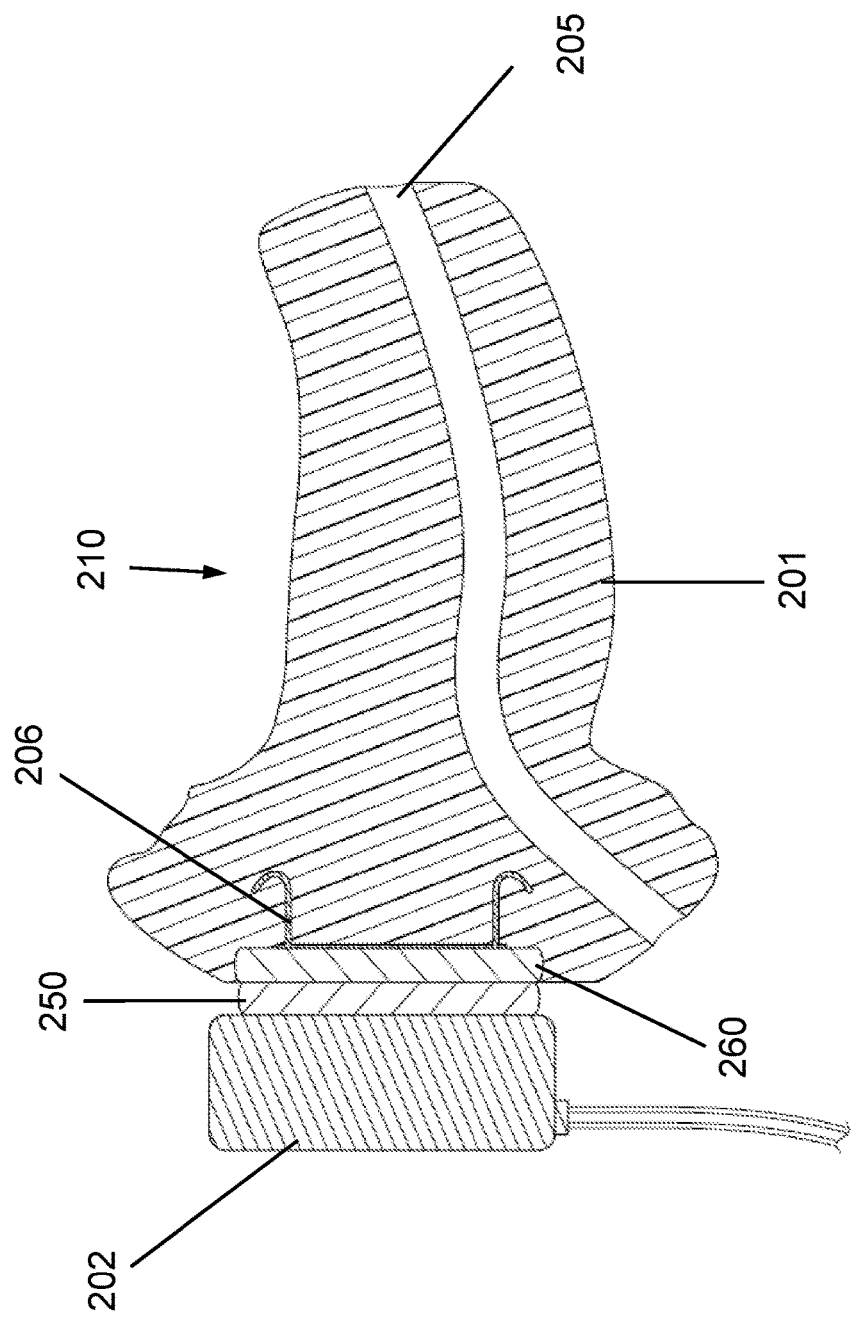
FIG. 9 is a schematic illustration of an exemplary device, where the earpiece comprises a disk magnet at its proximal end which is magnetically coupled to a magnet of opposite polarity attached to a vibratory motor. This figure shows that the two disc magnets have precisely latched on to each other, and established a firm connection for vibratory energy transfer.

FIGS. 8A-C and FIG. 9 depicts an embodiment of the invention, wherein housing 201 of earpiece 210 is releasably coupled to an external vibration motor 202. For example, in one embodiment illustrated in FIG. 8A and FIG. 9, motor 202 comprises a magnet 250, and the proximal end of housing 201 comprises a magnet 260, where magnet 250 and magnet 260 are of opposite polarity, such that motor 202 can be coupled to earpiece 210. Thus, when in proximity, the magnet 250 and magnet 260 attract each other to attach motor 202 to earpiece 210. When activated, motor 202 transmits vibrational energy through housing 201 and delivers vibrational energy to the outer wall of housing 201, thereby providing vibratory stimuli to the skin in contact with earpiece 210. Motor 202 may be detached from earpiece 210 by sliding magnet 250 and magnet 260 relative to each other. Magnet 250 and magnet 260 may be attached to motor 202 and housing 201 using any mechanism known in the art, including but not limited to, adhesives, magnetic anchors, and the like. For example, as shown in FIG. 9 and FIG. 10, earpiece 210 comprises an anchor 206 attached to magnet 260 to aid in securing magnet 260 to housing 201. Magnet 250 and magnet 260 may be of any suitable type and size, as known in the art. For example, in one embodiment, magnet 250 and magnet 260 are neodynium disk magnets. Other high-powered types of magnets may be used as understood by those having ordinary skill in the art. In one embodiment, the magnet 250 and magnet 260 have a diameter of about 2-10 mm and a thickness of about 0.1-10 mm. In one embodiment, magnet 250 and magnet 260 exert pull force of about 0.5 to 10 lbs. In certain embodiments, motor 202 is coupled to wire 204 which allows for communication with a control unit and/or a computing device, as described elsewhere herein. Further, in one embodiment, earpiece 210 comprises a duct 205 running through the length of housing 201 to establish air pressure equilibrium. Further, in one embodiment, and as shown for example in FIGS. 8B and 8C, earpiece 210 comprises a vibrational rod 3' which may aid in transmitting vibrational energy throughout earpiece 210, as described elsewhere herein.

The releasable coupling of motor 202 to earpiece 210 allows for earpiece 210 to remain inserted within the ear of the subject, without being connected to motor 202 or to a control unit, if desired by the subject. Further, as motor 202 is not embedded within housing 201, the size or geometry of motor 202 is not particularly limited to the types of motors which can fit within housing 201. While the present embodiment is exemplified by way of magnetic coupling of the motor, a skilled artisan would recognize that the motor may be releasably coupled to the earpiece housing using alternative methodology, including but not limited to hook and ladder coupling, adhesive coupling, and the like.

In one embodiment, the present invention provides a device and system comprising a computing device in communication with one or more of the control units, earpieces, and/or motors described elsewhere herein. For example, in one embodiment, one or more of the control units are programmed by a computing device, such as a remote desktop, laptop, smartphone, tablet, wearable computing device, and the like, which is in wired or in wireless communication with the control unit. The computing device may comprise software which may establish the amplitude, pulse rate, pulse burst duration, and interburst interval, and any other parameter of applied vibrational energy, as desired. In one embodiment, the computing device outputs a synchronizing signal to store on a recording device when concurrent physiological monitoring (necessary for those subjects who have concurrent autonomic pathology with migraine pain). In certain embodiments, the computing device may be in direct communication, either via wired or wireless communication, with the inserted earpiece and/or the motor attached to or embedded within the earpiece.

In one embodiment, the present invention may be controlled directly by a wireless computing device, such as tablets, smartphones or other wireless digital/cellular devices that are network enabled and include a software application platform or portal providing a user interface as contemplated herein. The applications platform may be a local or remotely executable software platform, or a hosted internet or network program or portal. The computing devices may include at least one processor, standard input and output devices, as well as all hardware and software typically found on computing devices for storing data and running programs, and for sending and receiving data over a network. The communications network between the computing device and the vibrator component can be a wide area network and may be any suitable networked system understood by those having ordinary skill in the art, such as, for example, an open, wide area network (e.g., the internet), an electronic network, an optical network, a wireless network, personal area networks such as Bluetooth, a physically secure network or virtual private network, and any combinations thereof. In certain embodiments, the computing device comprises a display suitable for visual representation of system control and status. The communications between the computing device and the control unit and/or vibration motor may be conducted via any wireless based technology, including, but not limited to radio signals, near field communication systems, hypersonic signal, infrared systems, cellular signals, GSM, and the like.

In certain embodiments, the computing device comprises a software application used for the input of stimulation parameters, delivery of stimulation parameters, storage of stimulation protocols, storage of user information, and the like. The software application platform may be a local or remotely executable software platform, or a hosted internet or network program or portal.

The software platform includes a graphical user interface (GUI) for inputting stimulation parameters, modulating function of the control unit and vibration motor, and for displaying information regarding the historical or real-time functionality of the device, as well as historical or real-time pain perception. In certain embodiments, wireless communication for information transfer to and from the computing device may be via a wide area network and may form part of any suitable networked system understood by those having ordinary skill in the art for communication of data to additional computing devices, such as, for example, an open, wide area network (e.g., the internet), an electronic network, an optical network, a wireless network, personal area networks such as Bluetooth, a physically secure network or virtual private network, and any combinations thereof. Such an expanded network may also include any intermediate nodes, such as gateways, routers, bridges, internet service provider networks, public-switched telephone networks, proxy servers, firewalls, and the like, such that the network may be suitable for the transmission of information items and other data throughout the system.

As would be understood by those skilled in the art, the computing device may be wirelessly connected to the expanded network through, for example, a wireless modem, wireless router, wireless bridge, and the like. Additionally, the software platform of the system may utilize any conventional operating platform or combination of platforms (Windows, Mac OS, Unix, Linux, Android, etc.) and may utilize any conventional networking and communications software as would be understood by those skilled in the art.

To protect data, an encryption standard may be used to protect files from unauthorized interception over the network. Any encryption standard or authentication method as may be understood by those having ordinary skill in the art may be used at any point in the system of the present invention. For example, encryption may be accomplished by encrypting an output file by using a Secure Socket Layer (SSL) with dual key encryption. Additionally, the system may limit data manipulation, or information access. Access or use restrictions may be implemented for users at any level. Such restrictions may include, for example, the assignment of user names and passwords that allow the use of the present invention, or the selection of one or more data types that the subservient user is allowed to view or manipulate.

In certain embodiments the network provides for telemetric data transfer to and from the control unit, vibration motor, and computing device. For example, data transfer can be made via any wireless communication technology, including, but not limited to radio signals, near field communication systems, hypersonic signal, infrared systems, cellular signals, GSM, and the like. In some embodiments, data transfer is conducted without the use of a specific network. Rather, in certain embodiments, data are directly transferred to and from the control unit and computing device via systems described above.

The software may include a software framework or architecture that optimizes ease of use of at least one existing software platform, and that may also extend the capabilities of at least one existing software platform. The software provides applications accessible to one or more users (e.g. patient, clinician, etc.) to perform one or more functions. Such applications may be available at the same location as the user, or at a location remote from the user. Each application may provide a graphical user interface (GUI) for ease of interaction by the user with information resident in the system. A GUI may be specific to a user, set of users, or type of user, or may be the same for all users or a selected subset of users. The system software may also provide a master GUI set that allows a user to select or interact with GUIs of one or more other applications, or that allows a user to simultaneously access a variety of information otherwise available through any portion of the system. Presentation of data through the software may be in any sort and number of selectable formats. For example, a multi-layer format may be used, wherein additional information is available by viewing successively lower layers of presented information. Such layers may be made available by the use of drop down menus, tabbed pseudo manila folder files, or other layering techniques understood by those skilled in the art.

The software may also include standard reporting mechanisms, such as generating a printable results report, or an electronic results report that can be transmitted to any communicatively connected computing device, such as a generated email message or file attachment. Likewise, particular results of the aforementioned system can trigger an alert signal, such as the generation of an alert email, text or phone call, to alert a patient, doctor, nurse, emergency medical technicians, or other health care provider of the particular results.

Treatment Methods

The present invention may bring substantial relief of pain to a wide range of headache syndromes, and does so non-invasively and rapidly to the affected person with minimal medical intervention after initial fitting and testing of the device within the subject's external ears. The present invention may reduce pain within seconds of administration, without use of pharmaceutical agents that may have deleterious cognitive, arousal, mood or motoric side effects. Further, the present invention avoids use of electrical stimulation, paralytic muscle agents, such as Botox, or invasive surgery, such as lesions to cranial nerve nuclei to eliminate pain, or vascular decompression surgery to relieve blood vessel pressure from excitable nerves causing pain as are currently used for migraine. The present invention may also be used to "train" brain activity to reduce the incidence of epochs of headache pain, or to minimize the debilitating character of those headache episodes. Such "training" is evidenced by the gradual decline in need to use the method in a group of affected patients; both episodes of pain and incidence of such symptoms as lack of salivation decline with repeated use of the method.

The present invention provides a method of treating or preventing pain in a subject in need thereof, comprising positioning a vibratory earpiece within at least one ear of a subject and applying vibrational energy to at least a portion of the skin of at least one of the auditory canal, auricle and concha of the subject's ear. The method thus stimulates one or more sensory fibers of at least one of cranial nerve 5, cranial nerve 7, cranial nerve 9, and cranial nerve 10, spinal nerve C2, and spinal nerve C3 of the subject.

In some embodiments, a comfortable and effective vibration amplitude and rate level may first be established for the subject by a medical practitioner. Afterwards, the subject may use the device when needed to reduce pain, or, with longer vibration periods, prevent occurrence of epochs of pain. In some embodiments, the subject may report on the efficacy of the device by regularly completing pain scale information. In certain embodiments, a subject being treated, caregiver, and/or medical practitioner may program the vibratory stimulation pattern delivered by the device to best treat the subject. For example, the subject, caregiver, and/or medical practitioner may alter one or more of amplitude, pulse rate, pulse burst duration, interburst interval and any other parameter of applied vibrational energy, as desired. For example, the parameters may be altered based upon observed or reported changes in pain intensity, frequency, duration, and the like.

The present methods may be carried out on any subject. In certain embodiments, the subject is a mammal. In one embodiment, the subject is a human. However, the invention is not limited to use in humans.

The method of the present invention may be used to treat or prevent pain in a subject including, for example pain in the head, neck, oral cavity, or face of the subject. For example, the method may be used to treat or prevent disorders including, but not limited to, primary headache, secondary headache, cluster headaches, migraine, trigeminal neuralgia, glossopharyngeal neuralgia, hemicrania continua, stabbing headache, cough headache, sinus headache, tension headache, exertional headache, sex headache, hypnic headache, cervicogenic headache, radiation pain, burning mouth syndrome, fibromyalgia, and the like. In one embodiment, the method reduces the intensity of pain. In one embodiment, the method reduces the duration of pain. In one embodiment, the method reduces the frequency of the onset of pain. In certain embodiments, the method is used to treat or prevent migraine-associated disorders, including, but not limited to, vertigo, dizziness, hypotension, hypertension, depression, anxiety, bipolar disorder, and the like. In certain embodiments, the method is used to treat or prevent one or more symptoms of migraine or headache pain, including, but not limited to, vision disturbances, altered mood, irritability, fatigue, muscle pain, nasal congestion, constipation, diarrhea, sensitivity to light, sensitivity to smell, sensitivity to touch, hypertension, hypotension, speech disturbances, hallucinations, delusions, weakness, nausea, vomiting, cognitive difficulties, and the like. In certain embodiments, the method reduces one or more of the intensity, duration, or frequency of pain or migraine related symptoms.

In certain embodiments, the method may be used to correct movement disorders of the head and speech.

In certain embodiments, present invention provides a method for induction of sleep. For example, in one embodiment, the method induces quiet sleep followed by rapid eye movement sleep within 15 minutes, and can be used to induce such sleep states.

In one embodiment, the present invention provides a method of treating and preventing xerostomia or dry mouth syndrome. Dry mouth syndrome frequently accompanies neural radiation injury following radiation for oncology, or damage to oral nerves following dental procedures or trauma. Use of the method resulted in gradual increasing of time when salivation was present with repeated interventions by the method, in some cases resulting in remission. The syndrome can result in excessive tooth decay, halitosis, impaired swallowing, and difficulty in chewing and processing certain foods, and greatly interferes with quality of life. Xerostomia treated or prevented by way of the present invention, may occur for a variety of reasons, including but not limited to, dehydration, radiation, side effect of medication, sicca syndrome, Sjogren's syndrome, alcohol use, tobacco use, recreational drug use, diabetes, and the like. It is demonstrated herein that vibrational stimulation of the ear canal of the subject increases salivation in subjects afflicted with xerostomia. Without being bound to any particular theory, the salivation benefit from the present method presumably stems from activation of parasympathetic fibers which accompany branches of cranial nerves 5, 7, and 9, and comprise part of cranial nerve 10. Parasympathetic nerves accompany 5, 7, and 9 on their path to secretory glands, including salivatory glands, and cranial nerve 10 supplies parasympathetic fibers to the pharynx for secretory glands. Vibratory stimulation will cross-activate the accompanying parasympathetic fibers, and also exacerbate neural activation simulating sensory input from the oral cavity that would trigger salivary output.

Figure 19:
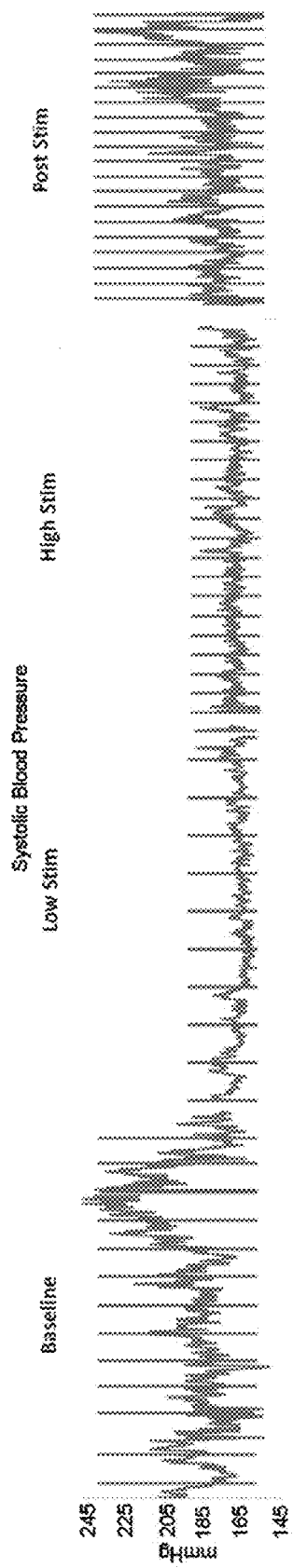
FIG. 19 is a set of traces, depicting the decline of beat-by-beat systolic blood pressure in a severely hypertensive patient with concurrent migraine during stimulation. Vertical red lines represent consecutive minutes (minute intervals vary, since baseline and stimulation periods differ, and an attempt was made to maximize collection time). "Low Stim" refers to mild vibration at 1.5 volts; "High Stim" refers to stronger vibration at 3 volts. BP declines to a nadir 4 minutes after low stim onset, remains low with high stimulation, and rises again after 14 minutes post stim. Migraine pain declined during treatment as well. All measures were taken with the patient in a sitting, unmoving position.
Figure 20:
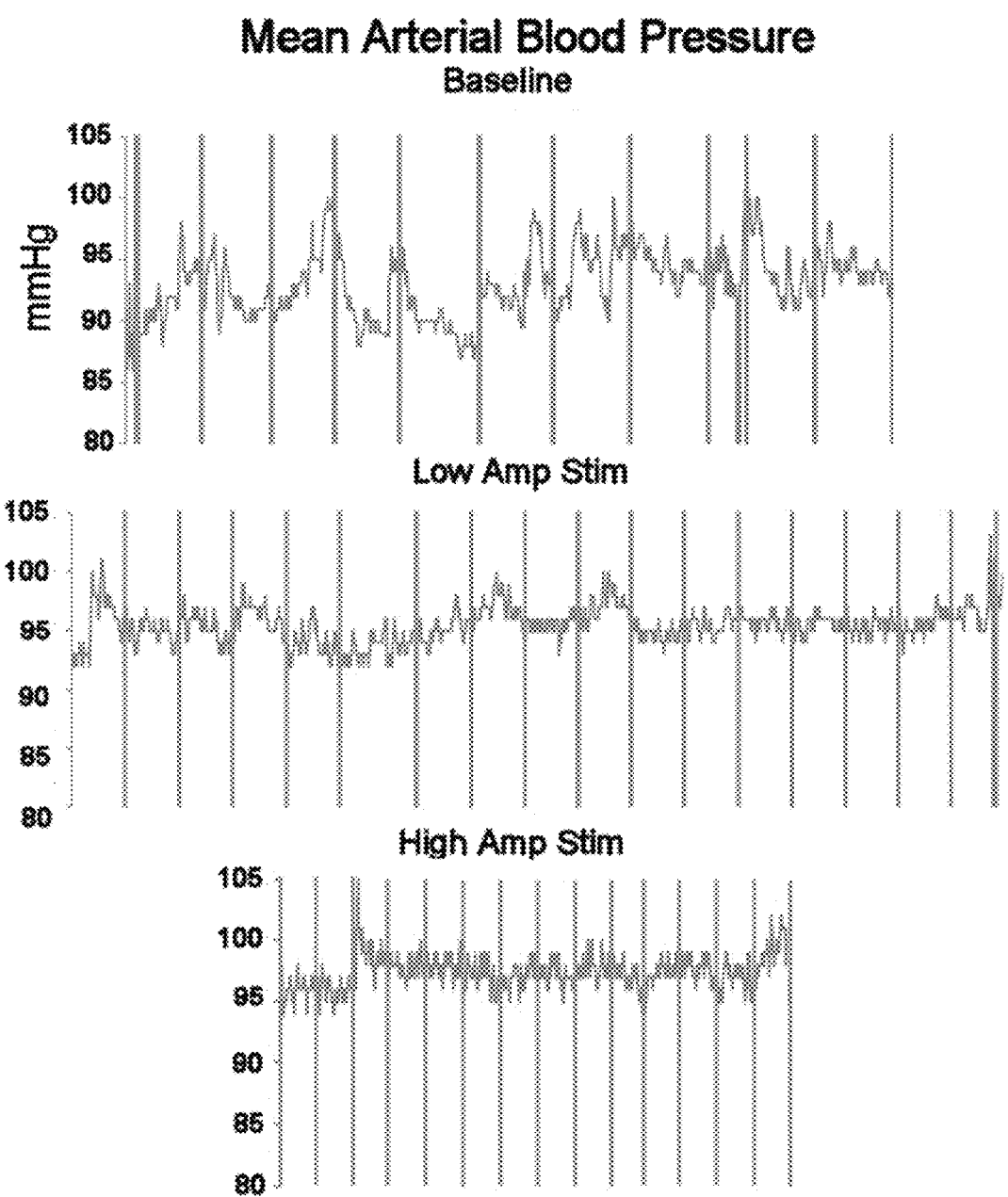
FIG. 20 is a set of traces depicting the effect of stimulation on the beat-by-beat mean arterial blood pressure of a subject with orthostatic hypotension (characterized by syncope with head turning or arising from a seated position). The condition was resolved with the intervention to the point that the subject was able to abandon wheelchair use. The top "Baseline" recording depicts the low, but wildly varying blood pressure at rest. The middle "Low Amp Stim" tracing recording depicts beat-by-beat blood pressure at low stimulation (1.5 volts to vibratory motor); blood pressure is mildly elevated from baseline, but significantly stabilizes by the tenth minute of stimulation. The lowest tracing depicts beat-by-beat blood pressure at high stimulation (3.0 volts to vibratory motor). Blood pressure continues to be elevated over baseline conditions, with no wild fluctuations.

In one embodiment, the present invention provides a method of treating and preventing momentary hypotension in a subject in need thereof. For example, in certain instances stimulation via the device and system of the invention reduces variation in blood pressure and restores proper variation in cardiac R-R interval induced by vagal and $9^{th}$ cranial nerve processes. The $9^{th}$ cranial nerve innervates the carotid baroreceptors, which regulate blood pressure and activation of a branch of the $9^{th}$ nerve can modify that innervation. In addition, cranial nerve 10 innervates the aortic baroreceptors, and carry that information to the nucleus of the solitary tract, a central nervous system responsible for integrating blood pressure. Thus stimulation of cranial nerve 10 can modify blood pressure sensing by the aortic baroreceptors, and modify activity of the solitary tract nucleus to influence blood pressure. In one embodiment, the present invention provides a method of rapidly lowering excessive high blood pressure by means of stimulation of those two nerves, as is shown in FIG. 19. In another embodiment, stimulation can improve orthostatic hypotension by reducing momentary large variation in, and modestly elevating, blood pressure (FIG. 20).

In another embodiment, stimulation of cranial nerves 5, 7, 9, and 10, and spinal nerve C3 may significantly impact breathing pathologies, including the three most common sources of respiratory deficiencies, namely obstructive sleep apnea, periodic breathing, and hypoventilation, including central apnea (hypoventilation) induced in congenital central hypoventilation syndrome (CCHS), spinal cord injury, or apnea of prematurity.

For example, hypoventilation, the reduced ventilation that occurs in multiple syndromes, results in inadequate flow of air to the lungs from underperforming respiratory musculature, total cessation of all respiratory muscle action (central apnea), or intermittent breathing with breathing pauses (periodic breathing). Accordingly, the device, system and methods of the present invention may be used to treat subjects with conditions involving hypoventilation. The effectiveness of the present invention in such instances stems from the capability to modify activity in nerves that can markedly enhance breathing. For example, motor components of spinal nerve C3 form part of the phrenic nerve output, the principal nerve which drives the diaphragm, and stimulation of C3 sensory components can elicit activity in C3 motor elements. This activation may thus enhance breathing in hypoventilating subjects, a major concern in spinal cord injury during sleep, in some genetic syndromes, such as congenital central hypoventilation, and a range of other pathologies with weakened muscles or impaired neural drive to respiratory muscles. Normalization of breathing patterns in a hypoventilating subject with concurrent obstructive sleep apnea, as described herein, may also be obtained with use of the present invention.

For example, obstructive sleep apnea, the loss of upper airway muscle activity in the presence of continued diaphragmatic movements during sleep, is a syndrome that affects nearly 12 percent of the U.S. population, and results in substantial injurious cardiovascular, memory, cognitive, and blood glucose changes. The objective is to activate the upper airway muscles just before, and during inspiratory diaphragmatic activity, so that the upper airway does not close, as it does in obstructive sleep apnea. Accordingly, the present invention may trigger several sequences that "trick" the brain to activate the upper airway muscles. Stimulation of cranial nerve 10 may provoke sensory activity acting as if that activity was lung inflation, which will normally trigger the upper airway muscles to activate, dilating the upper airway, and preventing airway obstruction. Activation of cranial nerves 5, 7 and 9 also triggers nerve action that is perceived in the brain as airflow, a necessary component to "trick" the brain to stimulate upper airway muscles to avoid upper airway obstruction and maintain breathing.

The present invention may also be used to treat other breathing patterns that do not meet the usual definition of obstructed breathing, periodic breathing, or hypoventilation. For example, Multiple Systems Atrophy, in addition to obstructive sleep apnea and hypoventilation, also shows stridor, a narrowing of the upper airway characterized by unique high-frequency breathing sounds and limited airflow, a characteristic resulting from failed action of the posterior cricoarytenoid (PCA) vocal cord dilators (or hyperactivity of the opposing laryngeal closure muscles). Such failure indicates failure of cranial nerve 10 motor fibers to those muscles. The present invention, by stimulating cranial nerve 10 afferents, may directly enable correction of the failed programming of the upper airway musculature in Multiple Systems Atrophy.

Further, stimulation of cranial nerves 9 and 10, because they provide sensory nerves to the carotid body, a principal sensor for blood pressure (barosensor), may be performed to modify blood pressure; cranial nerve 10, which supplies the aortic nerves and cardiac plexus, can also affect blood pressure regulation. In another embodiment, the presence of afferent nerves from the 9th and 10th cranial nerves allows the present invention to modify signals from the barosensors served by the 9th cranial nerve and the cardiac slowing mediated by the 10th cranial nerve. Activation of the 10th (vagus) nerve, in general, has an anti-arrhythmogenic effect. Several forms of arrhythmia, especially atrial fibrillation found in obstructive sleep apnea, may be modified by stimulation of the 9th and 10th cranial nerves in the external auditory canal by the present invention.

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the present invention and practice the claimed methods. The following working examples therefore, specifically point out the preferred embodiments of the present invention, and are not to be construed as limiting in any way the remainder of the disclosure.

Example 1

In an experimental example, pain perception was examined in 18 subjects with chronic migraine or trigeminal pain which was inadequately controlled by current medications. A plastic earpiece containing a vibrating element was placed within the external ear canal of each subject. Vibration induced by low-level battery power from a remote stimulation device was initiated by each subject after 1 min of onset of pain, and continued for a period of 20-50 minutes. Ratings of pain severity were made by the patient, using an appropriate pain assessment scale. A second, but closely related study examined the incidence of migraine episodes in subjects who have repetitive and quantifiable onsets of migraine. These subjects received vibratory stimuli for 20-50 when they begin to experience migraine pain. The change in perceived pain, as well as the time between episodes of migraine pain was tabulated.

Subjects

Eighteen adult subjects, aged 19-76 years or age, diagnosed with moderate-to-severe migraine by a UCLA headache pain physician were recruited. Subjects were in otherwise good health, with representation by sex in the same ratio as condition representation, i.e. 4 males and 14 females. Race, sex, or national origin were not reasons for exclusion. Subjects with cardiovascular, especially those with cardiac arrhythmia, or major psychiatric disorders were excluded. Subjects were recruited by notices in the UCLA Headache Clinic.

Earpiece

Subjects had a custom earpieces constructed from inert silicone using conventional earpiece impression procedures, as commonly employed for hearing aids. The custom earpieces were constructed with sufficient safeguards, using cotton or other soft material at the medial portion of the external ear canal so that no injury to the tympanic membrane occurs, while still ensuring appropriate contact for stimulation at appropriate sites in the canal. The impressions were taken by an audiologist experienced in such procedures at a time prior to experimentation, with the procedure requiring approximately 20 minutes. The impression was converted to a positive mold containing the vibration device, and the subject returned for the experimental session.

Vibration Device

The vibration device consists of two components: 1) the custom earpiece, derived from an impression of the subject's left and right ears; these earpieces contain the vibration motors attached to a small metal rod which contacts the inner wall of the silicone mold on an area proximal to the receptive field on the ear canal tissue, and 2) a programmed stimulation device (control unit) containing a low voltage battery which powers the vibration motors. The vibration motor is similar to those found in powered toothbrushes or cell phones. The stimulation device is programmed via Bluetooth signals from an Android tablet or smartphone.

Autonomic and Respiratory Monitoring

Migraine episodes can be accompanied by aberrant autonomic patterns, such as nausea and cardiovascular changes. Any intervention which may modify migraine episodes may also alter autonomic aspects, and thus, these autonomic characteristics need to be evaluated during such interventions. Prior to any assessment of pain or vibration characteristics, the subject was seated in a comfortable chair, and instrumented with a thoracic pressure band to assess thoracic wall movements; ECG electrodes on the medial thoracic wall near the heart, on the lateral thoracic wall opposite the first electrode, and at the caudal end of the sternum; and a pulse oximeter on the index finger. Leads from those electrodes were connected to a SOMNOtouch RESP device (SOMNOmedics, Coral Gables, Fla.) for collection of ECG, thoracic wall movements, oxygen saturation, pulse transit time, and beat-by-beat systolic and diastolic blood pressure (determined from pulse transit time). Conventional cuff blood pressure measurements was determined on the subject prior to, and at the end of data collection, to calibrate the SOMNOmedics blood pressure device. The device allows continuous monitoring of signals on a small display screen so that abnormal variation can be readily observed. All data was subsequently transferred from the device to computing device.

Pain Scale

The Numerical Rating Score for Pain (NRS) was completed by the subject at onset of the first trial, when the patient reports that he/she is undergoing a moderate-to-severe headache, and at the end of the experimental session for the day. This scale is a uni-dimensional single item scale that provides an easy-to-administer and score scale that allows subjects to rate pain from 0-10 in intensity, and is widely used in the pain field (Hawker, G. A. Mian, S., Kendzerska, T., French, M. Measures of adult pain. Arthritis Care and Research 2011; 63:S240-S252). It requires about 1-2 minutes to administer.

The following pain scale (1-10) is used to classify pain from the subjects:

1: Very mild=Very light, barely noticeable pain, like a mosquito bite or a poison ivy itch. Most of the time you never think about the pain.

2: Uncomfortable=Minor pain, like lightly pinching the fold of skin between the thumb and first finger with the other hand, using the fingernails.

3: Tolerable=Very noticeable pain, like an accidental cut, a blow to the nose causing a bloody nose, or a doctor giving you a shot. The pain isn't so strong that you can't get used to it.

4: Distressing=Strong, deep pain, like an average toothache, the initial pain from a bee sting, or minor trauma like stubbing your toe real hard. So strong that you notice the pain all the time and can't completely adapt.

5: Very distressing=Strong, deep, piercing pain, such as a sprained ankle when you stand on it wrong, or mild back pain. Not only do you notice the pain all the time, you are now so preoccupied with managing it that your normal lifestyle is curtailed.

6: Intense=Strong, deep, piercing pain, so strong that it seems to partially dominate your senses, causing you to think somewhat unclearly. Comparable to a bad non-migraine headache combined with several bee stings or a bad back pain.

7: Very intense=Same as 6, except that the pain completely dominates your senses causing you to think unclearly about half the time.

8: Utterly horrible=Pain so intense that you can no longer think clearly at all, and have often undergone severe personality change if the pain has been present for a long time. Comparable to childbirth or a real bad migraine.

9: Excruciating unbearable=Pain so intense that you can't tolerate it and demand pain killers or surgery, no matter what the side effects or risk.

10: Unimaginable unspeakable=Pain so intense that you will go unconscious shortly.

Acute Vibration

Following completion of the pain rating, the earpiece was inserted, and the subject questioned on comfort of the device without vibration. Following affirmation of comfort, a 120-160 Hz vibratory signal was applied, initially at low amplitude, and upon confirmation of comfort levels, with increasing levels until the subject reports mild discomfort from the local vibration. The amplitude was then lowered to a level congruent with the subject reports of a comfortable setting. Typically, trials begin with a low amplitude level (1.5 volts) for 10 minutes, after which the trial continues with a higher amplitude (3.0 volt) signal. Before, and at the end of the trial, the pain scale is administered. The physiological electrodes and the earpiece is then removed. The subject is queried on general pain perceptions, any other affective perceptions, and preferences on whether they would like to use the device again.

Figure 14:
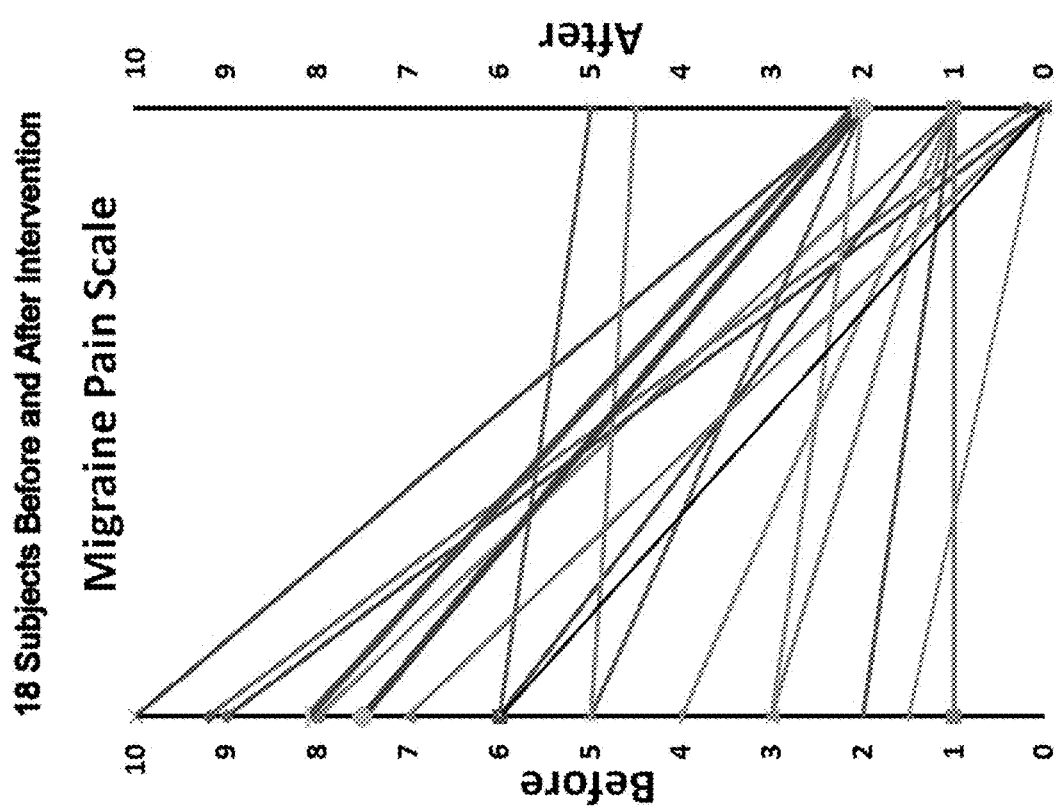
FIG. 14 is a graph depicting the results of the most substantial reported pain reduction for 18 different subjects with migraine or trigeminal neuropathy pain after use of the device for less than 50 minutes of the present invention. Of the 18 subjects, 17 showed reduction in reported pain, and one showed no change. In some cases, the pain reduction was substantial (e.g., on a pain scale of 0 to 10, where a rating of 10 is so severe that the subject is at risk to go unconscious, 9 to 0 on two subjects, 10 to 2 on one subject, 8 to 0, 8 to 1, and 8 to 2 on three additional subjects). That outcome is statistically significant ($p<0.0001$, paired t-test).

The outcomes of the pain ratings for all 18 subjects are shown in FIG. 14. Of the 18 subjects, 17 showed reduction in reported pain, and one showed no change. In some cases, the pain reduction was substantial (e.g., on a pain scale of 0 to 10, where a rating of 10 is so severe that the subject is at risk to go unconscious, 9 to 0 on two subjects, 10 to 2 on one subject, 8 to 0, 8 to 1, and 8 to 2 on three additional subjects). That outcome is statistically significant ($p<0.0001$, paired t-test).

Example 2: Severe Migraine and Trigeminal Neuropathy

A 38 year old female subject with severe migraine and orthostatic hypotension, with a secondary diagnosis of post-traumatic stress syndrome for approximately 3 years was treated using the device of the present invention. The subject's pain had been poorly controlled by opiates and antidepressants.

The parameters of stimulation were as with all 18 subjects; an initial baseline with no stimulation, a 10 minute low amplitude (1.5 volt, 120 Hz vibration), followed by a 20 minute high amplitude (3.0 volts) vibration, and a 5 minute post stimulation baseline.

Figure 15:
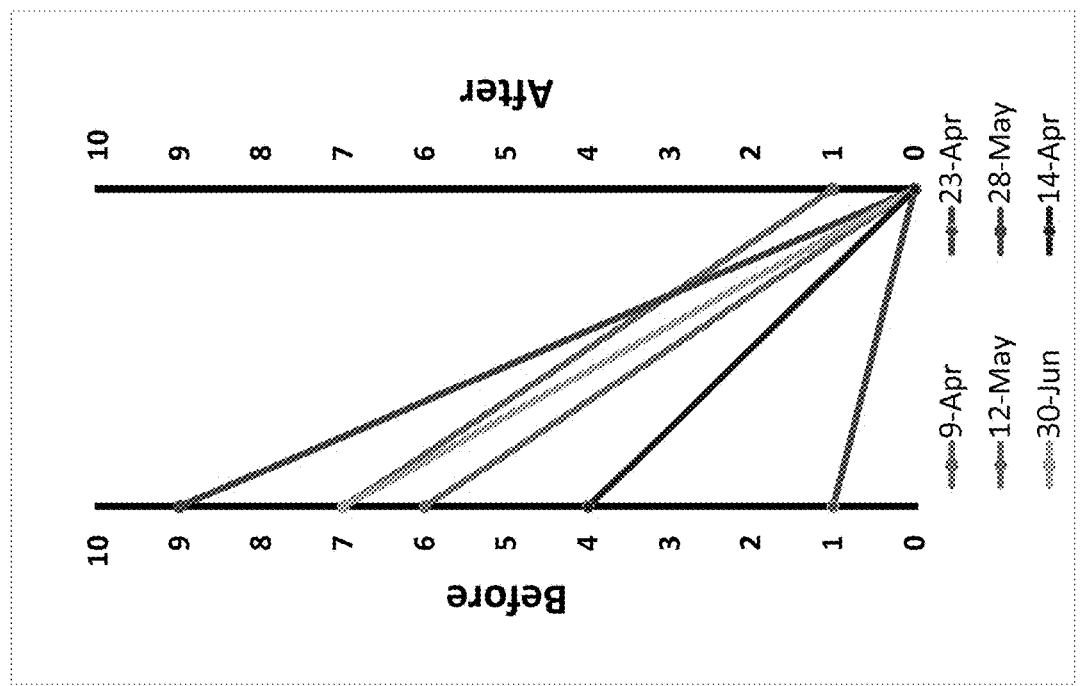
FIG. 15 is a graph depicting the reduction of pain reported by a subject with severe migraine after use of the device of the present invention on 6 successive occasions; the dates of interventions are shown below the graph.

The subject received vibratory stimulation of the ear canal using the present device on 6 separate treatment sessions. As shown in FIG. 15, reported pain decreased at each session, with pain reported at 0 or 1 after each session.

A 19 year old female subject with severe migraine for approximately 2 years was treated using the device of the present invention. The subject's pain had been uncontrolled by medication.

Figure 16:
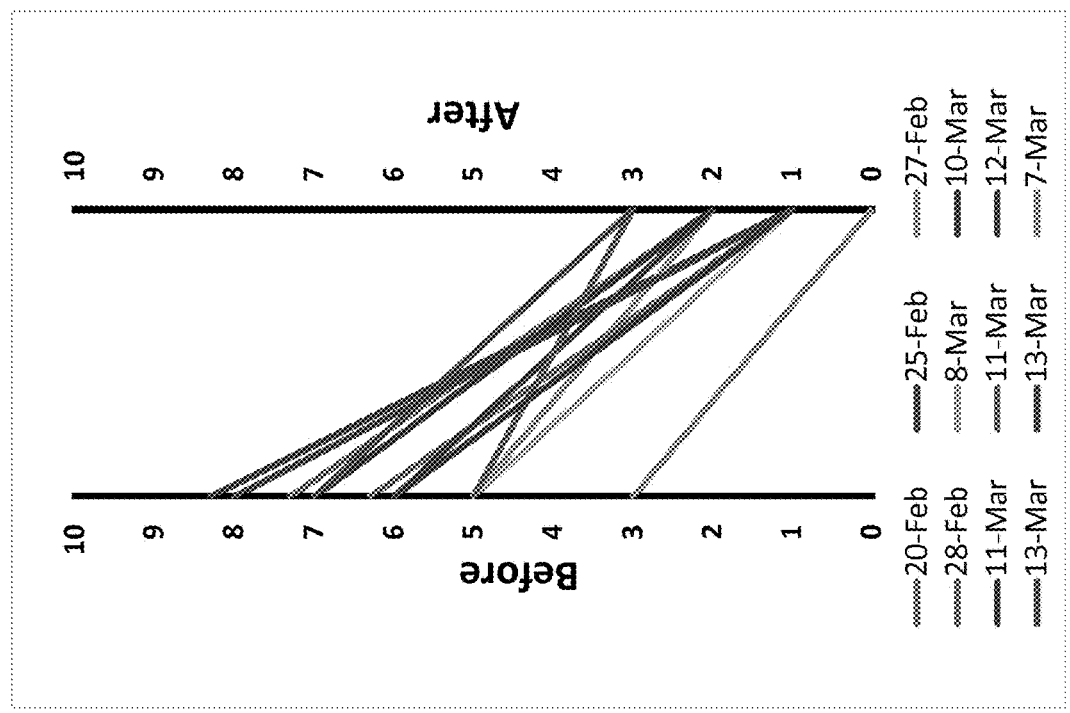
FIG. 16 is a graph depicting the reduction of pain reported by a subject with severe migraine after use of the device of the present invention on 12 successive occasions.

The subject received vibratory stimulation of the ear canal using the present device on 12 separate treatment sessions, using parameters of 5 minute baseline with no stimulation, 10 minutes of low amplitude (1.5 volt) 120 Hz stimulation, followed by 20 minutes of high amplitude (3.0 volts), and a subsequent no stimulation post baseline. As shown in FIG. 16, reported pain decreased at each session.

Figure 17:
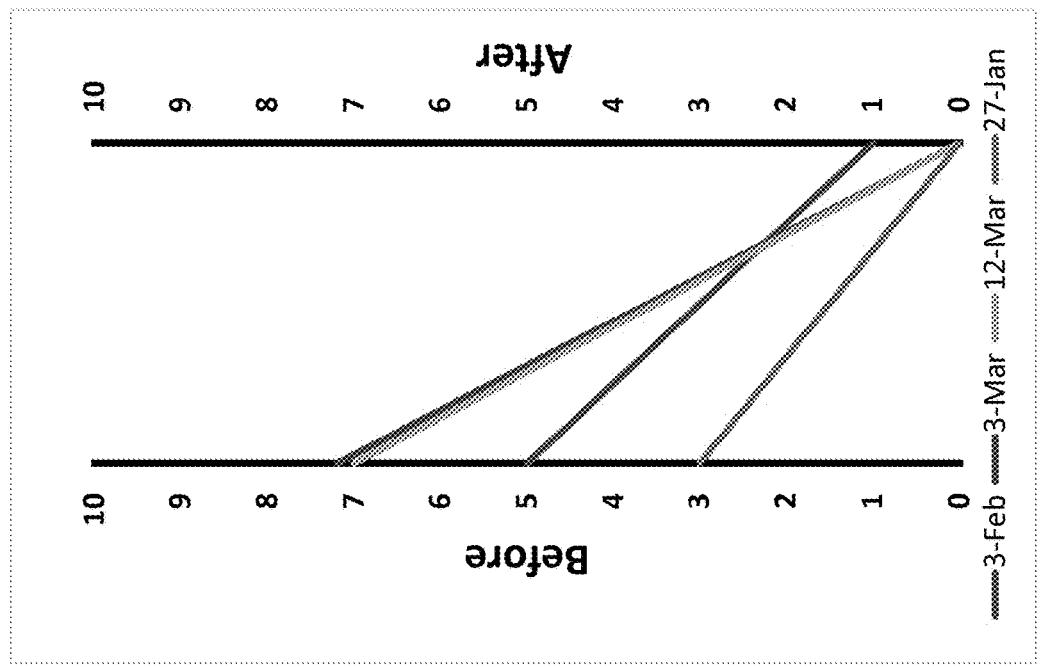
FIG. 17 is a graph depicting the reduction of pain reported by a subject with trigeminal neuropathy after use of the device of the present invention on 4 successive occasions.

A 48 year old male subject with trigeminal neuropathy for approximately 5 years was treated using the device of the present invention. The trigeminal neuropathy of the subject stemmed from a root canal procedure. The subject's pain had been poorly controlled by Tegretol (carbamazepine). The subject received 10 minutes of low amplitude (1.5 volts to the motor) vibratory stimulation (120 Hz) of both ear canals followed by high amplitude (3.0 volts to the motor) vibration for 20 minutes using the present device on 4 separate treatment sessions. As shown in FIG. 17, reported pain decreased at each session, with pain reported at 0 or 1 after each session. In addition, profuse salivation and tearing occurred, a great benefit for the patient who also suffered from dry mouth.

FIG. 14 depicts the results of vibratory stimulation of 18 different subjects with migraine and/or trigeminal neuropathy. It is demonstrated that the pain decreased in 17 subjects after stimulation, with pain remaining unchanged in only one subject.

Example 3: Burning Mouth Syndrome

A 73 year old female subject with burning mouth syndrome, characterized by burning sensation of the tongue, pain in the upper and lower mucosa of the anterior oral cavity, and paresthesia in the lips, for approximately 2.5 years was treated using the device of the present invention. The subject's pain had been poorly controlled by Gabapentine.

Figure 18:
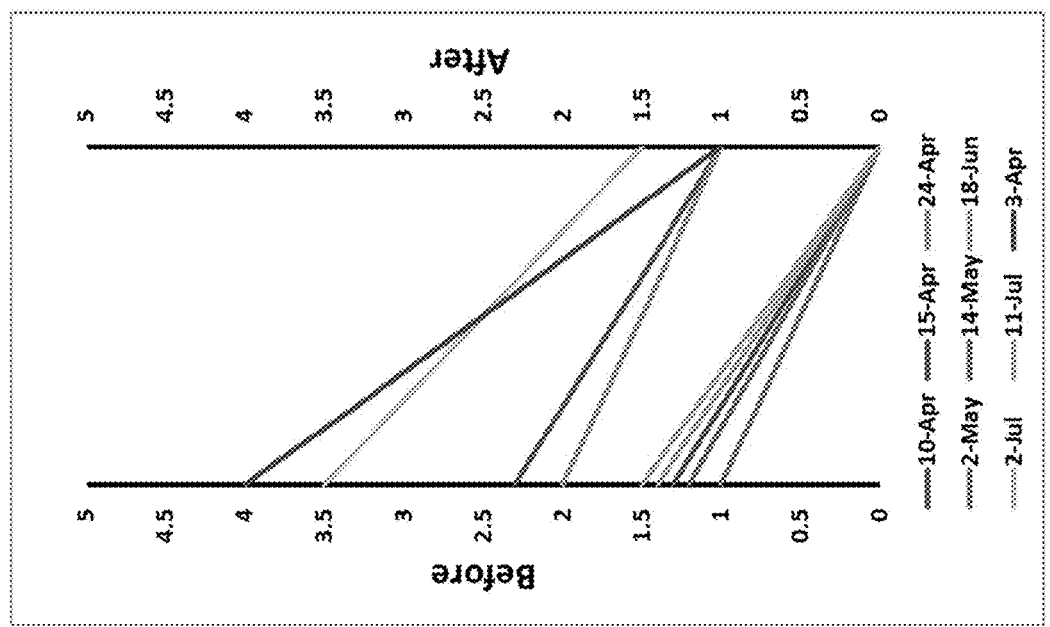
FIG. 18 is a graph depicting the reduction of pain reported by a subject with burning mouth syndrome after use of the device of the present invention on 9 successive occasions. Further interventions have ended, since pain has been resolved.

The subject received 120 Hz vibratory stimulation of both ear canals using the present device on 9 separate treatment sessions. Stimulation was comprised of an initial period of 10 minutes of low amplitude (1.5 volt to the motor), followed by high stimulation (3.0 volts of the motor). As shown in FIG. 18, the reported pain decreased at each session, with longer intervals between sessions, beginning initially with four days before re-intervention was required, extending to 2-3 weeks between necessary interventions; pain is now entirely gone, and she no longer returns for sessions. In addition, salivation increased following each intervention.

Example 4: Hypotension

For safety reasons, all pain interventions were accompanied by simultaneous recording of heart rate, thoracic and abdominal breathing movements, oxygen saturation, and beat-by-beat blood pressure. These recordings provided the serendipitous findings of long-term and momentary changes in breathing, blood pressure and cardiac variability (R-R intervals) associated with stimulation.

The findings indicate a substantial reduction in wide swings in blood pressure in a 38 year old female orthostatic hypotensive patient (being treated for migraine), to relatively stable variation, with an overall restoration to normotensive levels (FIG. 20). In addition, blood pressure returned to normal patterns of variation with breathing. The patient required use of a wheelchair, since turning of the head, or arising from a sitting position, resulted in syncope. Those fainting episodes were abolished by the third session; subsequently the patient abandoned wheelchair use.

Figure 21:
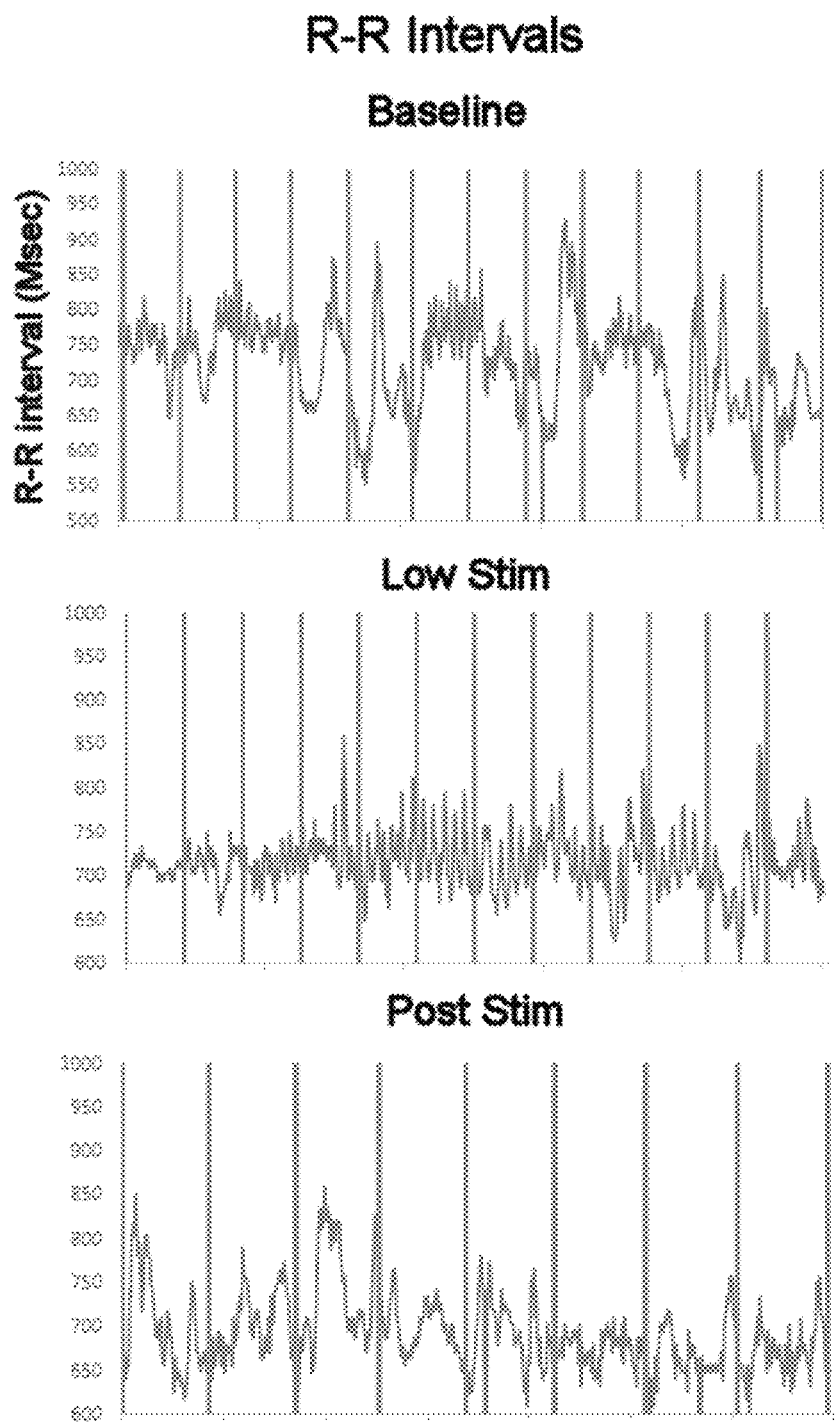
FIG. 21 is a set of recordings depicting the effect of stimulation on the cardiac R-R intervals (time between successive heart beats; an index of both rate and variability), of a subject with orthostatic hypotension. The top recording depicts R-R intervals at baseline, and shows a relatively slow rate (long intervals), and excessive slow variation, typical of intermittent sympathetic nervous system action. The middle tracing depicts R-R intervals at low stimulation (1.5 volts to vibratory motor); the tracing shows an overall faster rate (shorter intervals), and substantial periods of highly rhythmical respiratory-related variation, especially between minutes 5-7. Such respiratory modulation is mediated by the vagus (cranial nerve 10), and is considered protective against cardiac arrhythmia. The third recording depicts R-R intervals post-stimulation, with the cardiac patterning returning to highly variable large slow variation typically found with sympathetic action, and indicative of risk.

Cardiac R-R intervals, which showed wide variation during baseline pre-stimulation, showed a return to pronounced respiratory-related variation, i.e., marked high frequency variation, a pattern considered in the cardiovascular field as a vagally-mediated cardioprotective pattern (FIG. 21).

Example 5: Hypertension

A 72 year old male patient with dangerously high blood pressure and concurrent migraine pain underwent one session of stimulation. Systolic arterial pressure ranged up to 240 mmHg during baseline (FIG. 19), but rapidly declined (within 4 minutes; 4 vertical red lines on FIG. 19) during low amplitude (1.5 volt) stimulation to values near 150 mmHg, and remained at these lower levels during high amplitude (3 volt) stimulation; on cessation of all stimulation, systolic pressure rose again to values near 245 mmHg. Continuous vibration at 120 Hz was applied, with no variation in pulse characteristics, except for amplitude change from 1.5 to 3 volts for low (10 minutes of low amplitude) and 20 minutes of high stimulation. Migraine pain was reduced from an initial level 3 to 0.

Example 6: Salivation

A frequent accompaniment of trigeminal neuropathy is poor salivation, or xerostomia (dry mouth syndrome), and frequently occurs after radiation treatment for oral oncology, or after trauma to the trigeminal or $7^{th}$ cranial nerve. The condition leads to enhanced tooth decay, and greatly impairs quality of life, since eating particular foods, swallowing, and taste are greatly affected. The condition also tends to elicit reflexive tic-like oral movements, such as lip smacking to overcome dryness. The subjects underwent the usual stimulation parameters of no stimulation during a 10 minute baseline, 10 minutes of 120 Hz vibration at low (1.5 volt) level, 20-30 minutes of high (3.0 volt) level, and a short post baseline. Seven of the 18 patients reported the dry mouth condition, one from radiation treatment, and another from cervical nerve trauma, and the remaining from other oral nerve trauma; two had reflexive lip smacking movements (common in dry mouth syndrome to maintain hydration). All reported improvement, and in some cases, substantial improvement, which included partial resolution of the reflexive lip motor signs. The condition is difficult to quantitatively measure, but one subject who used Pilocarpine, an agent to enhance saliva, reported that she was able to avoid use of the agent initially for one day, and with successive interventions for 2-3 days, and most recently, for 4 days. Another patient reported reduction of the dry mouth for one week after the initial intervention, which corresponded to reduction in burning mouth pain over the same time period. Another patient, who received radiation therapy for cancer of the parotid, had severe migraine, dry mouth, and impaired speech. Pain diminished, salivation increased, and the subject's speech became more articulate.

Example 7: Sleep Induction

Twelve of the 18 subjects fell into quiet asleep during the stimulation; sleep onset occurred as early as 12 minutes following onset of stimulation. The stimulation parameters were the usual parameters of 120 Hz vibration at 1.5 volt (low level) and 3.0 volt (high level) for 10 and 20-30 minutes, respectively. The sleep events all appeared during interventions carried out in the daytime, at times when the subjects would not normally sleep. On three occasions, the person accompanying the subject expressed amazement that sleep was occurring, given the subjects' usual behavior at home or work. Three different subjects entered rapid eye movement (REM) sleep in addition to the initial quiet sleep, as evidenced by peripheral limb twitches, erratic breathing, rapid eye movements, and self-report of dreaming. A substantial proportion of the subjects reported very deep sleep on the night of the intervention. Those subjects who did not sleep, uniformly reported a very relaxed state at the conclusion of the intervention.

Example 8: Sleep Disordered Breathing

Two subjects, one 38 year old female, the other a 72 year old male, had obstructive sleep apnea, the male with very severe obstructive apnea (apnea hyponea index >30), documented by polysomnographic recordings at a sleep center, in addition to migraine pain. Both subjects slept during the stimulation, offering the potential to evaluate the effectiveness of the method in preventing apnea. Both subjects entered REM sleep after quiet sleep, and one subject showed repeated episodes of sleeping on multiple stimulation trials. No evidence of airway obstruction appeared in either subject. Stimulation parameters were 120 Hz vibration, 1.5 volt low level for 10 minutes, and 20-30 minutes of 3.0 volt high level. The absence of obstructive apnea, which invariable appears quickly when an individual enters quiet or REM sleep, suggests a protective role for the stimulation, as proposed by the theoretical outline above.

Example 9: Migraine-Associated Vestibular and Visual Disturbances

A 75 year old female with migraine pain for greater than 5 years also showed severe vestibular and visual symptoms, expressed as an inability to visually focus, and an inability to maintain stability while head-turning or single-foot standing. She underwent 10 interventions using the standard parameters of 120 Hz vibration at 1.5 volts and 3.0 volts for 10 and 20 minutes, respectively. Although she was unable to show improvements in the initial intervention, pain was reduced. After 10 interventions, vestibular and visual signs improved; she was able to easily stand on one foot for >15 sec, head turning did not precipitate collapse, and visual focusing significantly improved.

The disclosures of each and every patent, patent application, and publication cited herein are hereby incorporated herein by reference in their entirety.

While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations

What is claimed is:

1. A device for stimulating mechanoreceptors of one or more sensory fibers of at least one nerve, comprising:
   an earpiece comprising a housing molded substantially to fit within the external ear canal and configured to contact the concha of a subject's ear, the housing having a distal end, a proximal end, and a length therebetween; and
   a vibratory motor embedded within the housing, wherein the vibratory motor transmits vibrational energy to the outer wall of housing;
   wherein the device is configured to stimulate one or more mechanoreceptors of sensory fibers of cranial nerve 9 when the housing is positioned in the external ear canal.

2. The device of claim 1, wherein the vibratory motor is connected to and powered by a control unit.

3. The device of claim 2, wherein the control unit is controlled by a computing device.

4. The device of claim 3, wherein the computing device controls the control unit wirelessly.

5. The device of claim 1, wherein the earpiece is a customized silicon-plastic mold.

6. The device of claim 1 further comprising a vibrating rod having a substantially flat plate and an elongated arm, wherein the plate is in contact with the vibratory motor and the elongated arm extends away from the vibratory motor.

7. The device of claim 6, wherein the elongated arm of the vibrating rod is an angled rod having between a 35-40° bend to match the curvature of the subject's ear canal.

8. The device of claim 1, further comprising a hollow air duct running from the distal end to the proximal end of the earpiece housing.

9. The device of claim 1, wherein the device is further configured to stimulate mechanoreceptors served by one or more sensory fibers of at least one nerve selected from the group consisting of cranial nerve 5, cranial nerve 7, cranial nerve 10, spinal nerve C2, and spinal nerve C3.

10. The device of claim 1, wherein the device is further configured to simultaneously stimulate mechanoreceptors served by one or more sensory fibers of cranial nerve 5, cranial nerve 7, cranial nerve 10, spinal nerve C2, and spinal nerve C3.

11. A device for stimulating mechanoreceptors serving one or more sensory fibers of at least one nerve, comprising:
   an earpiece comprising a housing molded substantially to fit within the external ear canal and configured to contact the concha of a subject's ear, the housing having a distal end, a proximal end, and a length therebetween; and
   a vibratory motor releasably coupled to the housing, wherein the vibratory motor transmits vibrational energy to the outer wall of housing;
   wherein the device is configured to stimulate one or more mechanoreceptors of sensory fibers of cranial nerve 9 when the housing is positioned in the external ear canal.

12. The device of claim 11, wherein the vibratory motor is connected to and powered by a control unit.

13. The device of claim 12, wherein the control unit is controlled by a computing device.

14. The device of claim 13, wherein the computing device controls the control unit wirelessly.

15. The device of claim 11, wherein the earpiece comprises a magnet embedded within the housing and wherein the device further comprises a magnet attached to the vibratory motor, such that the magnet of the motor releasably couples to the magnet of the housing.

16. The device of claim 11, wherein the earpiece is a customized silicon-plastic mold.

17. The device of claim 11 further comprising a vibrating rod having an elongated arm which extends away from the releasably coupled vibratory motor.

18. The device of claim 17, wherein the elongated arm of the vibrating rod is an angled rod having between a 35-40° bend to match the curvature of the subject's ear canal.

19. The device of claim 11, further comprising a hollow air duct running from the distal end to the proximal end of the earpiece housing.

20. The device of claim 11, wherein the device is configured to stimulate mechanoreceptors served by one or more sensory fibers of at least one nerve selected from the group consisting of cranial nerve 5, cranial nerve 7, cranial nerve 10, spinal nerve C2, and spinal nerve C3.

21. The device of claim 11, wherein the device is configured to simultaneously stimulate mechanoreceptors served by one or more sensory fibers of cranial nerve 5, cranial nerve 7, cranial nerve 10, spinal nerve C2, and spinal nerve C3.

22. A method for non-invasively stimulating mechanoreceptors served by one or more sensory fibers of at least one nerve, comprising
   positioning a vibratory earpiece, comprising a housing having a distal end, a proximal end, and a length therebetween, within at least one ear of a subject; and
   stimulating one or more mechanoreceptors of sensory fibers of cranial nerve 9 by applying vibrational energy through the vibratory earpiece to at least a portion of the skin of at least one of the auditory canal, auricle, and concha of the subject's ear.

23. The method of claim 22, wherein the at least one nerve further comprises a nerve selected from the group consisting of cranial nerve 5, cranial nerve 7, cranial nerve 10, spinal nerve C2, and spinal nerve C3.

24. The method of claim 22, wherein mechanoreceptors served by one or more sensory fibers of each of a plurality of nerves are stimulated simultaneously by the vibrational energy.

25. The method of claim 22, wherein the method reduces pain in at least one of the head, face, mouth, or neck of the subject.

26. The method of claim 22, wherein the method enhances breathing of the subject.

27. The method of claim 22, the method normalizes blood pressure via stimulation of at least the $9^{th}$ and $10^{th}$ cranial nerves supplying the carotid sinus baroreceptors and aortic sensors.

28. The method of claim 22, wherein the method increases saliva production in the subject.

29. A non-invasive method of reducing headache pain in a subject, comprising the steps of:
   positioning a vibratory earpiece, comprising a housing having a distal end, a proximal end and a length therebetween, within at least one ear of a subject; and
   stimulating one or more mechanoreceptors of sensory fibers of cranial nerve 9 by applying vibrational energy through the vibratory earpiece to at least a portion of the skin of at least one of the auditory canal, auricle, and concha of the subject's ear.

30. The method of claim 29, wherein the at least one nerve further comprises a nerve selected from the group consisting of cranial nerve 5, cranial nerve 7, cranial nerve 10, spinal nerve C2, and spinal nerve C3.

31. The method of claim 29, wherein mechanoreceptors served by one or more sensory fibers of a plurality of nerves selected from the group consisting of cranial nerve 5, cranial nerve 7, cranial nerve 10, spinal nerve C2, and spinal nerve C3 are stimulated simultaneously by the vibrational energy.

* * * * *